US010738338B2

(12) United States Patent
Callahan et al.

(10) Patent No.: US 10,738,338 B2
(45) Date of Patent: Aug. 11, 2020

(54) METHOD AND COMPOSITION FOR BIOCATALYTIC PROTEIN-OLIGONUCLEOTIDE CONJUGATION AND PROTEIN-OLIGONUCLEOTIDE CONJUGATE

(71) Applicant: The Research Foundation for The State University of New York, Binghamton, NY (US)

(72) Inventors: Brian Callahan, Binghamton, NY (US); Timothy Owen, Huntington, NY (US)

(73) Assignee: The Research Foundation for The State University, Binghamton, NY (US)

( * ) Notice: Subject to any disclaimer, the term of this patent is extended or adjusted under 35 U.S.C. 154(b) by 252 days.

(21) Appl. No.: 15/782,391

(22) Filed: Oct. 12, 2017

(65) Prior Publication Data

US 2018/0112245 A1  Apr. 26, 2018

Related U.S. Application Data

(60) Provisional application No. 62/409,655, filed on Oct. 18, 2016.

(51) Int. Cl.
| | |
|---|---|
| *C12P 21/00* | (2006.01) |
| *A61K 47/55* | (2017.01) |
| *A61K 47/54* | (2017.01) |
| *C12N 9/10* | (2006.01) |
| *C07K 1/107* | (2006.01) |

(52) U.S. Cl.
CPC ............. *C12P 21/00* (2013.01); *A61K 47/55* (2017.08); *A61K 47/554* (2017.08); *C07K 1/1077* (2013.01); *C12N 9/1029* (2013.01); *C12Y 201/01041* (2013.01)

(58) Field of Classification Search
CPC ...... A61K 47/28; A61K 47/6807; C12P 21/00
USPC ........................................................ 530/300
See application file for complete search history.

(56) References Cited

U.S. PATENT DOCUMENTS

| | | | |
|---|---|---|---|
| 3,773,919 A | 11/1973 | Boswell et al. |
| 6,544,772 B1 | 4/2003 | Glenn et al. |
| 6,620,585 B1 | 9/2003 | Zyskind |
| 6,773,706 B2 | 8/2004 | Schneewind et al. |
| 6,790,448 B2 | 9/2004 | Xu et al. |
| 6,838,239 B1 | 1/2005 | Zyskind |
| 6,841,154 B2 | 1/2005 | Foster et al. |
| 6,896,887 B2 | 5/2005 | Leenhouts et al. |
| 6,908,994 B1 | 6/2005 | Rich et al. |
| 6,936,252 B2 | 8/2005 | Gilbert et al. |
| 6,994,982 B1 | 2/2006 | Watt et al. |
| 7,067,248 B2 | 6/2006 | Hruby et al. |
| 7,067,621 B2 | 6/2006 | Yeaman et al. |
| 7,067,639 B2 | 6/2006 | Leenhouts et al. |
| 7,101,692 B2 | 9/2006 | Schneewind et al. |
| 7,125,698 B2 | 10/2006 | Glenn et al. |
| 7,179,458 B2 | 2/2007 | Chang et al. |
| 7,183,101 B2 | 2/2007 | Arigoni et al. |
| 7,195,763 B2 | 3/2007 | Xu et al. |
| 7,238,489 B2 | 7/2007 | Schneewind et al. |
| 7,270,969 B2 | 9/2007 | Watt et al. |
| 7,312,076 B2 | 12/2007 | Chang et al. |
| 7,348,420 B2 | 3/2008 | Klaenhammer et al. |
| 7,371,719 B2 | 5/2008 | Stupp et al. |
| 7,384,775 B2 | 6/2008 | Zagursky et al. |
| 7,390,526 B2 | 6/2008 | Stupp et al. |
| 7,452,679 B2 | 11/2008 | Stupp et al. |
| 7,455,992 B2 | 11/2008 | Klaenhammer et al. |
| 7,456,011 B2 | 11/2008 | Liu et al. |
| 7,485,710 B2 | 2/2009 | Reinscheid et al. |
| 7,491,690 B2 | 2/2009 | Stupp et al. |
| 7,534,761 B1 | 5/2009 | Stupp et al. |
| 7,534,876 B2 | 5/2009 | Klaenhammer et al. |
| 7,538,209 B2 | 5/2009 | Klaenhammer et al. |
| 7,541,039 B2 | 6/2009 | Leenhouts et al. |
| 7,544,661 B2 | 6/2009 | Stupp et al. |
| 7,554,021 B2 | 6/2009 | Stupp et al. |
| 7,615,616 B2 | 11/2009 | Hook et al. |
| 7,632,515 B2 | 12/2009 | Gilbert et al. |
| 7,635,487 B2 | 12/2009 | Meinke et al. |
| 7,648,708 B2 | 1/2010 | Gilbert et al. |
| 2007/0082866 A1 | 4/2007 | Zlotnick et al. |
| 2007/0117197 A1 | 5/2007 | Chang et al. |
| 2007/0128210 A1 | 6/2007 | Olmsted et al. |
| 2007/0128211 A1 | 6/2007 | Olmsted et al. |
| 2007/0128229 A1 | 6/2007 | Olmsted et al. |
| 2007/0172495 A1 | 7/2007 | Klaenhammer et al. |
| 2007/0190029 A1 | 8/2007 | Pardoll et al. |
| 2007/0190063 A1 | 8/2007 | Bahjat et al. |
| 2007/0207170 A1 | 9/2007 | Dubensky et al. |
| 2007/0207171 A1 | 9/2007 | Dubensky et al. |
| 2007/0218075 A1 | 9/2007 | Matsuka et al. |
| 2007/0248581 A1 | 10/2007 | Chen et al. |
| 2007/0253964 A1 | 11/2007 | Zlotnick et al. |
| 2007/0258955 A1 | 11/2007 | Klaenhammer et al. |
| 2007/0286866 A1 | 12/2007 | Van Ginkel et al. |

(Continued)

OTHER PUBLICATIONS

Chaltin et al., Bioconjugate Chem., 2005, 16, 827-836. (Year: 2005).*

*Primary Examiner* — James H Alstrum-Acevedo
*Assistant Examiner* — Kaipeen E Yang
(74) *Attorney, Agent, or Firm* — Hoffberg & Associates; Steven M. Hoffberg

(57) ABSTRACT

A composition comprising a polypeptide ligated to an oligonucleotide through a sterol linker. A method of ligating a polypeptide to an oligonucleotide, comprising a polypeptide having a hedgehog steroyl transferse catalytic domain at the C-terminal of the polypeptide with an electrophilic residue, e.g., glycine, between polypeptide and the hedgehog steroyl transferse catalytic domain, and a steroylated oligonucleotide in solution, and permitting a reaction to cleave the hedgehog steroyl transferse catalytic domain from the polypeptide while ligating the steroylated oligonucleotide to the glycine at the C-terminal of the polypeptide. The oligonucleotide may be, for example, a therapeutic, diagnostic, or affinity ligand.

24 Claims, 8 Drawing Sheets

Specification includes a Sequence Listing.

(56) References Cited

U.S. PATENT DOCUMENTS

| | | |
|---|---|---|
| 2008/0031877 A1 | 2/2008 | Covacci et al. |
| 2008/0038287 A1 | 2/2008 | Meinke et al. |
| 2008/0050361 A1 | 2/2008 | Heinrichs et al. |
| 2008/0064079 A1 | 3/2008 | Hoess et al. |
| 2008/0089899 A1 | 4/2008 | Gilbert et al. |
| 2008/0171059 A1 | 7/2008 | Howland et al. |
| 2008/0175857 A1 | 7/2008 | Gilbert et al. |
| 2008/0220441 A1 | 9/2008 | Birnbaum et al. |
| 2008/0248522 A1 | 10/2008 | Seefeldt et al. |
| 2008/0254070 A1 | 10/2008 | Gilbert et al. |
| 2008/0260768 A1 | 10/2008 | Gilbert et al. |
| 2009/0022753 A1 | 1/2009 | Olmsted et al. |
| 2009/0035780 A1 | 2/2009 | McCarthy et al. |
| 2009/0041744 A1 | 2/2009 | Ostergaard et al. |
| 2009/0075839 A1 | 3/2009 | Zagursky et al. |
| 2009/0088337 A1 | 4/2009 | Gill et al. |
| 2009/0088372 A1 | 4/2009 | Roy et al. |
| 2009/0092582 A1 | 4/2009 | Bogin et al. |
| 2009/0117113 A1 | 5/2009 | Bensi et al. |
| 2009/0130115 A1 | 5/2009 | Hook et al. |
| 2009/0148408 A1 | 6/2009 | Chang et al. |
| 2009/0155304 A1 | 6/2009 | Liu et al. |
| 2009/0176967 A1 | 7/2009 | Stennicke |
| 2015/0197538 A1 | 7/2015 | Janetka et al. |
| 2015/0197734 A1 | 7/2015 | Ma et al. |
| 2015/0203834 A1 | 7/2015 | Iverson et al. |
| 2015/0210756 A1 | 7/2015 | Torres et al. |
| 2015/0216960 A1 | 8/2015 | Zlotnick et al. |
| 2015/0231228 A1 | 8/2015 | Amara et al. |
| 2015/0232518 A1 | 8/2015 | Foster et al. |
| 2015/0232541 A1 | 8/2015 | Fenn et al. |
| 2015/0232560 A1 | 8/2015 | Heindl et al. |
| 2015/0232561 A1 | 8/2015 | Fenn et al. |
| 2015/0241440 A1 | 8/2015 | Fasan et al. |
| 2015/0246024 A1 | 9/2015 | Richter et al. |
| 2015/0253335 A1 | 9/2015 | Burkart et al. |
| 2015/0258210 A1 | 9/2015 | Van Delft et al. |
| 2015/0259389 A9 | 9/2015 | Berka et al. |
| 2015/0259397 A1 | 9/2015 | Lee et al. |
| 2015/0259431 A1 | 9/2015 | Stemmer et al. |
| 2015/0266943 A1 | 9/2015 | Chhabra et al. |
| 2015/0273040 A1 | 10/2015 | McAdow et al. |
| 2015/0273042 A1 | 10/2015 | Maione et al. |
| 2015/0274800 A1 | 10/2015 | Schellenberger et al. |
| 2015/0284452 A1 | 10/2015 | Bremel et al. |
| 2015/0284477 A1 | 10/2015 | Chaikof et al. |
| 2015/0290362 A1 | 10/2015 | Douglas et al. |
| 2015/0291704 A1 | 10/2015 | Beck et al. |
| 2015/0305361 A1 | 10/2015 | Holz-Schietinger et al. |
| 2015/0306212 A1 | 10/2015 | Kahvejian et al. |
| 2015/0306218 A1 | 10/2015 | Nowinski et al. |
| 2015/0309021 A1 | 10/2015 | Birnbaum et al. |
| 2015/0315248 A1 | 11/2015 | Galeotti et al. |
| 2015/0320882 A1 | 11/2015 | Van Delft et al. |
| 2015/0329568 A1 | 11/2015 | Tuttle et al. |
| 2015/0329590 A1 | 11/2015 | Pentelute et al. |
| 2015/0335724 A1 | 11/2015 | Zlotnick et al. |
| 2015/0338579 A1 | 11/2015 | Fattinger |
| 2015/0343051 A1 | 12/2015 | Grandi et al. |
| 2015/0344862 A1 | 12/2015 | Schellenberger et al. |
| 2015/0346195 A1 | 12/2015 | Belmant et al. |

\* cited by examiner

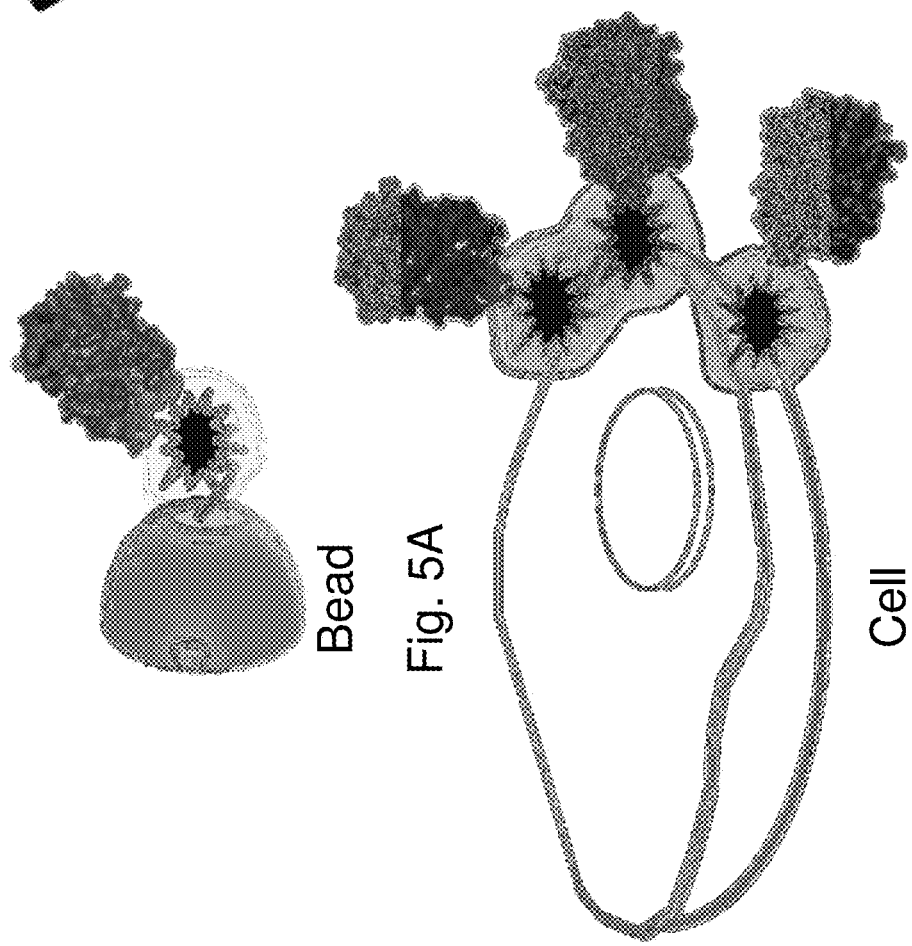
Fig. 5A Bead
Fig. 5B Antibody
Fig. 5C Cell

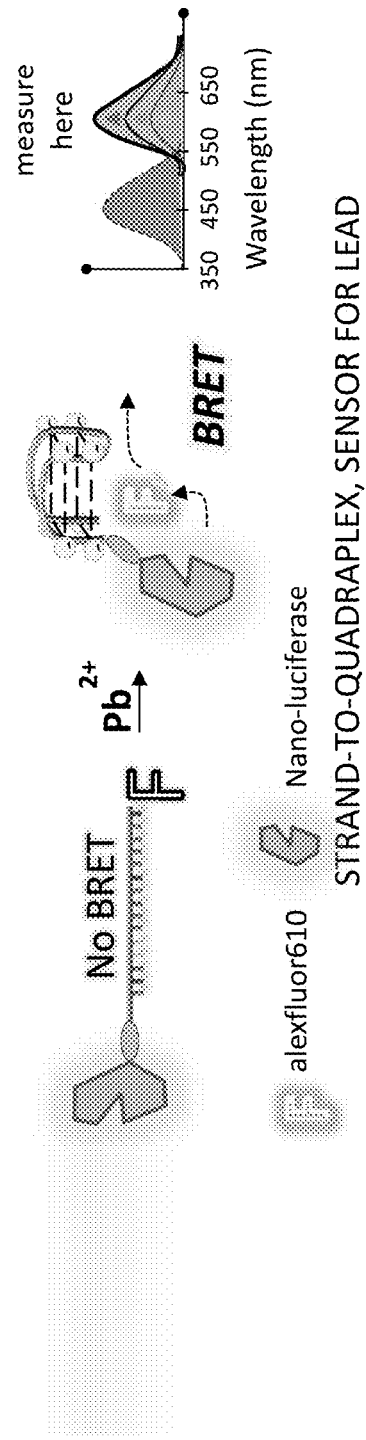
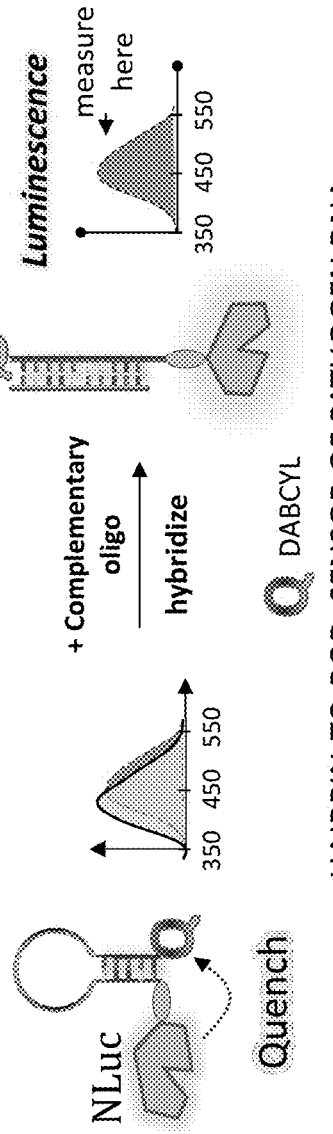
Fig. 6A — GENERAL SCHEME FOR CREATING ENZYME-APTAMER CONJUGATES
Fig. 6B — STRAND-TO-QUADRAPLEX, SENSOR FOR LEAD
Fig. 6C — HAIRPIN-TO-ROD, SENSOR OF PATHOGEN DNA

PROTEIN-OLIGO CONJUGATES FOR CELL-SPECIFIC DELIVERY

METHOD AND COMPOSITION FOR BIOCATALYTIC PROTEIN-OLIGONUCLEOTIDE CONJUGATION AND PROTEIN-OLIGONUCLEOTIDE CONJUGATE

CROSS REFERENCE TO RELATED APPLICATIONS

The present application is a non-provisional of, and claims benefit of priority from, U.S. Provisional Patent Application No. 62/409,655, filed Oct. 18, 2016, the entirety of which is expressly incorporated herein by reference.

FIELD OF INVENTION

The present invention relates to a protein catalyst for the attachment of diverse chemical matter, specifically oligonucleotides, to a specific amino acid in a polypeptide substrate.

BACKGROUND

All references cited herein are expressly incorporated herein by reference in their entirety.

Site-specific selective protein modification procedures have been useful for oriented protein immobilization, for studies of naturally occurring post-translational modifications, for creating antibody-drug conjugates, for the introduction of fluorophores and other small molecules on to proteins, for examining protein structure, folding, dynamics, and protein-protein interactions, and for the preparation of protein-polymer conjugates. One approach for protein labeling is to incorporate biorthogonal functionalities into proteins at specific sites via enzymatic reactions. The incorporated sites then support chemoselective reactions, since reactions may be defined that are inert to normal biological materials, and occur selectively when the biorthogonal component is present. Known enzymes for site-specific ligation include formylglycine generating enzyme, sialyltransferases, phosphopantetheinyltransferases, O-GlcNAc post-translational modification, sortagging, transglutaminase, farnesyltransferase, biotin ligase, lipoic acid ligase, and N-myristoyltransferase.

Proteins, comprised of varying numbers of 20 distinct amino acid residues, arranged in a specific sequence, are the primary mediators of biological processes in all organisms, from single cell bacteria to humans. Techniques to manipulate the function of proteins can therefore find important applications in fundamental science as well as medicine and engineering. For example, the capacity to attach therapeutic chemical matter to specific amino acid residues in an antibody can pave the way for targeted therapeutics (i.e. antibody-drug conjugates). In addition, techniques to attach fluorophores or other optical probes to specific amino acid residues of an enzyme can prove useful for investigating the protein's spatial and temporal function in a specific biological process.

Joining together chemical matter with a protein (i.e. conjugation) requires at a minimum two reactive functional groups, such as a nucleophile and an electrophile, that, when combined in solution, chemically unite. Because proteins are metastable, suitable conjugation chemistry must involve functional groups that react together selectively without appreciable side-reactions; tolerate the presence of water, salts, and buffers; proceed at reasonable rates at ambient temperature; and progress to near completion so as to minimize post-reaction workup of the conjugated protein.

There are several proteins with conjugation activity that have been developed commercially. Prominent examples: Halotag (Promega) www.promega.com/products/pm/halotag-technology/halotag-technology/ SNaP tag (New England Biolabs) www.neb.com/applications/protein-analysis-and-tools/proteinlabeling/protein-labeling-snap-clip Biotin ligase (Avidity) www.avidity.com/technologies/vitrobiotinylation-avitag-enzyme Sfp phosphopantetheinyltransferase (New England Biolabs) www.neb.com/products/p9302-sfp-synthase.

Of specific interest here is the conjugation of proteins to nucleic acids. Protein-DNA conjugates have been sought for fundamental and applied studies. In his 2010 review Niemeyer, Christof M. "Semisynthetic DNA-protein conjugates for biosensing and nanofabrication." Angewandte Chemie International Edition 49, no. 7 (2010): 1200-1216 (www.ncbi.nlm.nih.gov/pubmed/20091721), Niemeyer identified a number of emerging areas, including bioanalytics (i.e immunoPCR); DNA directed immobilization of proteins (biochips); nanofabrication of protein assemblies (DNA arrays); and synthesis of medicinal nanoparticles bearing therapeutic proteins and peptides.

Current methods to conjugate proteins with nucleic acids depend on "spontaneous" chemical conjugation chemistry, such as disulfide bond formation, as opposed to conjugation catalyzed by a biomolecule. No enzyme has been fully described that can directly conjugate proteins with nucleic acids. Rather, methods in current use require installing reactive functional groups on the protein and separately, on the nucleic acid (Neimeyer, www.ncbi.nlm.nih.gov/pubmed/20091721). The chemically modified protein and nucleic acid are combined in a single tube and allowed to react. Often, these bimolecular reactions proceed slowly, requiring 24 h or more, and generate modest yields, see for example (Barbuto, Scott, Juliana Idoyaga, Miguel Vila-Perelló, Maria P. Longhi, Gaëlle Breton, Ralph M. Steinman, and Tom W. Muir. "Induction of innate and adaptive immunity by delivery of poly dA:dT to dendritic cells." Nature chemical biology 9, no. 4 (2013): 250-256, www.ncbi.nlm.nih.gov/pubmed/23416331). More recently, strategies have emerged that make use of activated esters as well as click chemistry, and appear to increase the speed conjugation; however they suffer from a lack of specificity with respect to the site (i.e. amino acid residue) of protein-nucleic acid conjugation (www.ncbi.nlm.nih.gov/pubmed/26947912).

See (each of which is expressly incorporated herein by reference in its entirety):

(1) Hackenberger, C. P. R., and Schwarzer, D. (2008) Chemo-selective Ligation and Modification Strategies for Peptides and Proteins. Angew. Chem., Int. Ed. 47, 10030-10074.

(2) Rabuka, D. (2010) Chemoenzymatic methods for site-specific protein modification. Curr. Opin. Chem. Biol. 14, 790-796.

(3) Carrico, I. S. (2008) Chemoselective modification of proteins: hitting the target. Chem. Soc. Rev. 37, 1423.

(4) Wong, S. S., Jameson, D. M., and Wong, S. S. (2012) Chemistry of protein and nucleic acid cross-linking and conjugation, Taylor & Francis/CRC Press, Boca Raton.

(5) Fontana, A., Spolaore, B., Mero, A., and Veronese, F. M. (2008) Site-specific modification and PEGylation of pharmaceutical proteins mediated by transglutaminase. Adv. Drug Delivery Rev. 60, 13-28.

(6) Junutula, J. R., Raab, H., Clark, S., Bhakta, S., Leipold, D. D., Weir, S., Chen, Y., Simpson, M., Tsai, S. P., Dennis, M. S., Lu, Y., Meng, Y. G., Ng, C., Yang, J., Lee, C. C., Duenas, E., Gorrell, J., Katta, V., Kim, A., McDorman, K., Flagella, K., Venook, R., Ross, S., Spencer, S. D., Lee Wong, W., Lowman, H. B., Vandlen, R., Sliwkowski, M. X., Scheller, R. H., Polakis, P., and Mallet, W. (2008) Site-specific conjugation of a cytotoxic drug to an antibody improves the therapeutic index. Nat. Biotechnol. 26, 925-932.

(7) Gauchet, C., Labadie, G. R., and Poulter, C. D. (2006) Regio- and chemoselective covalent immobilization of proteins through unnatural amino acids. J. Am. Chem. Soc. 128, 9274-9275.

(8) Kochendoerfer, G. G. (2005) Site-specific polymer modification of therapeutic proteins. Curr. Opin. Chem. Biol. 9, 555-560.

(9) Chen, I., Howarth, M., Lin, W., and Ting, A. Y. (2005) Site-specific labeling of cell surface proteins with biophysical probes using biotin ligase. Nat. Meth. 2, 99-104.

(10) Köhn, M. (2009) Immobilization strategies for small molecule, peptide and protein microarrays. J. Pept. Sci. 15, 393-397.

(11) Wong, L. S., Khan, F., and Micklefield, J. (2009) Selective covalent protein immobilization: strategies and applications. Chem. Rev. 109, 4025-4053.

(12) Tiefenbrunn, T. K., and Dawson, P. E. (2010) Chemoselective ligation techniques: Modern applications of time-honored chemistry. Biopolymers 94, 95-106.

(13) Wu, B.-Y., Hou, S.-H., Huang, L., Yin, F., Zhao, Z.-X., Anzai, J.-I., and Chen, Q.
(2008) Oriented immobilization of immunoglobulin G onto the cuvette surface of the resonant mirror biosensor throughlayer-by-layer assembly of multilayer films. Mater. Sci. Eng., C 28, 1065-1069.

(14) Hermanson, G. T. (2008) Bioconjugate techniques, Academic Press, Amsterdam.

(15) Dixon, H. B. (1964) Transamination of peptides. Biochem. J. 92, 661-666.

(16) Wu, P., and Brand, L. (1997) N-terminal modification of proteins for fluorescence measurements. Meth. Enzymol. 278, 321-330.

(17) Scheck, R. A., Dedeo, M. T., Iavarone, A. T., and Francis, M. B. (2008) Optimization of a biomimetic transamination reaction. J. Am. Chem. Soc. 130, 11762-11770.

(18) Geoghegan, K. F., and Stroh, J. G. (1992) Site-directed conjugation of nonpeptide groups to peptides and proteins via periodate oxidation of a 2-amino alcohol. Application to modification at N-terminal serine. Bioconjugate Chem. 3, 138-146.

(19) Akgul, C., Moulding, D. A., White, M. R., and Edwards, S. W. (2000) In vivo localisation and stability of human Mcl-1 using green fluorescent protein (GFP) fusion proteins. FEBS Lett. 478, 72-76.

(20) Dundr, M., McNally, J. G., Cohen, J., and Misteli, T. (2002) Quantitation of GFP-fusion proteins in single living cells. J. Struct. Biol. 140, 92-99.

(21) Kanda, T., Sullivan, K. F., and Wahl, G. M. (1998) Histone-GFP fusion protein enables sensitive analysis of chromosome dynamics in living mammalian cells. Curr. Biol. 8, 377-385.

(22) Marguet, D., Spiliotis, E. T., Pentcheva, T., Lebowitz, M., Schneck, J., and Edidin, M. (1999) Lateral diffusion of GFP-tagged H2Ld molecules and of GFP-TAP1 reports on the assembly and retention of these molecules in the endoplasmic reticulum. Immunity 11, 231-240.

(23) Lisenbee, C. S., Karnik, S. K., and Trelease, R. N. (2003) Overexpression and mislocalization of a tail-anchored GFP redefines the identity of peroxisomal ER. Traffic 4, 491-501.

(24) De Graaf, A. J., Kooijman, M., Hennink, W. E., and Mastrobattista, E. (2009) Nonnatural amino acids for site-specific protein conjugation. Bioconjugate Chem. 20, 1281-1295.

(25) Wang, L., Xie, J., and Schultz, P. G. (2006) Expanding the genetic code. Annu. Rev. Biophys. Biomol. Struct. 35, 225-249.

(26) Chen, P. R., Groff, D., Guo, J., Ou, W., Cellitti, S., Geierstanger, B. H., and Schultz, P. G. (2009) A facile system for encoding unnatural amino acids in mammalian cells. Angew. Chem., Int. Ed. 48, 4052-4055.

(27) Guo, J., Melancon, C. E., Lee, H. S., Groff, D., and Schultz, P. G. (2009) Evolution of amber suppressor tRNAs for efficient bacterial production of proteins containing nonnatural amino acids. Angew. Chem., Int. Ed. 48, 9148-9151.

(28) Chatterjee, A., Xiao, H., and Schultz, P. G. (2012) Evolution of multiple, mutually orthogonal prolyl-tRNA synthetase/tRNA pairs for unnatural amino acid mutagenesis in *Escherichia coli*. Proc. Natl. Acad. Sci. U.S.A. 109, 14841-14846.

(29) Huisgen, R., Szeimies, G., and Mobius, L. (1967) Chemische Berichte-Recueil.
Chem. Ber. 100, 2494.

(30) Rostovtsev, V. V., Green, L. G., Fokin, V. V., and Sharpless, K. B. (2002) A stepwise huisgen cycloaddition process: copper(I)-catalyzed regioselective "ligation" of azides and terminal alkynes. Angew. Chem., Int. Ed. 41, 2596-2599.

(31) Kolb, H. C., Finn, M. G., and Sharpless, K. B. (2001) Click chemistry: diverse chemical function from a few good reactions. Angew. Chem., Int. Ed. 40, 2004-2021.

(32) Kohn, M., and Breinbauer, R. (2004) The Staudinger ligation • a gift to chemical biology. Angew. Chem., Int. Ed. 43, 3106-3116.

(33) Song, W., Wang, Y., Qu, J., Madden, M. M., and Lin, Q. (2008) A photoinducible 1,3-dipolar cycloaddition reaction for rapid, selective modification of tetrazole-containing proteins. Angew. Chem., Int. Ed. 47, 2832-2835.

(34) Song, W., Wang, Y., Qu, J., and Lin, Q. (2008) Selective functionalization of a genetically encoded alkene-containing protein via "photoclick chemistry" in bacterial cells. J. Am. Chem. Soc. 130, 9654-9655.

(35) De Araujo, A. D., Palomo, J. M., Cramer, J., Seitz, O., Alexandrov, K., and Waldmann, H. (2006) Diels-Alder ligation of peptides and proteins. Chem. Eur. J. 12, 6095-6109.

(36) De Araujo, A. D., Palomo, J. M., Cramer, J., Kohn, M., Schroder, H., Wacker, R., Niemeyer, C., Alexandrov, K., and Waldmann, H. (2006) Diels-Alder ligation and surface immobilization of proteins. Angew. Chem., Int. Ed. 45, 296-301.

(37) Liu, D. S., Tangpeerachaikul, A., Selvaraj, R., Taylor, M. T., Fox, J. M., and Ting, A. Y. (2012) Diels-Alder cycloaddition for fluorophore targeting to specific proteins inside living cells. J. Am. Chem. Soc. 134, 792-795.

(38) Blackman, M. L., Royzen, M., and Fox, J. M. (2008) Tetrazine ligation: fast bioconjugation based on inverse-electron-demand Diels-Alder reactivity. J. Am. Chem. Soc. 130, 13518-13519.

(39) Schoch, J., Wiessler, M., and Jaschke, A. (2010) Post-synthetic modification of DNA by inverse-electron-demand Diels-Alder reaction. J. Am. Chem. Soc. 132, 8846-8847.

(40) Cordes, E. H., and Jencks, W. P. (1962) Nucleophilic catalysis of semicarbazone formation by anilines. J. Am. Chem. Soc. 84, 826-831.

(41) Dirksen, A., Yegneswaran, S., and Dawson, P. E. (2010) Bisaryl hydrazones as exchangeable biocompatible linkers. Angew. Chem., Int. Ed., 2023-2027.

(42) Rashidian, M., Song, J. M., Pricer, R. E., and Distefano, M. D. (2012) Chemoenzymatic reversible immobilization and labeling of proteins without prior purification. J. Am. Chem. Soc. 134, 8455-8467.

(43) Miller, L. W., and Cornish, V. W. (2005) Selective chemical labeling of proteins in living cells. Curr. Opin. Chem. Biol. 9, 56-61.

(44) Sunbul, M., and Yin, J. (2009) Site specific protein labeling by enzymatic posttranslational modification. Org. Biomol. Chem. 7, 3361.

(45) Roeser, D., Preusser-Kunze, A., Schmidt, B., Gasow, K., Wittmann, J. G., Dierks, T., von Figura, K., and Rudolph, M. G. (2006) A general binding mechanism for all human sulfatases by the formylglycine-generating enzyme. Proc. Natl. Acad. Sci. U.S.A. 103, 81-86.

(46) Rush, J. S., and Bertozzi, C. R. (2008) New aldehyde tag sequences identified by screening formylglycine generating enzymes in vitro and in vivo. J. Am. Chem. Soc. 130, 12240-12241.

(47) Wu, P., Shui, W., Carlson, B. L., Hu, N., Rabuka, D., Lee, J., and Bertozzi, C. R. (2009) Site-specific chemical modification of recombinant proteins produced in mammalian cells by using the genetically encoded aldehyde tag. Proc. Natl. Acad. Sci. U.S.A. 106, 3000-3005.

(48) Rabuka, D., Rush, J. S., deHart, G. W., Wu, P., and Bertozzi, C. R. (2012) Site-specific chemical protein conjugation using genetically encoded aldehyde tags. Nat. Protoc. 7, 1052-1067.

(49) Bertozzi, C. R., and Kiessling, L. L. (2001) Chemical glycobiology. Science 291, 2357-2364.

(50) Angata, T., and Varki, A. (2002) Chemical diversity in the sialic acids and related alpha-keto acids: an evolutionary perspective. Chem. Rev. 102, 439-469.

(51) Bork, K., Horstkorte, R., and Weidemann, W. (2009) Increasing the sialylation of therapeutic glycoproteins: the potential of the sialic acid biosynthetic pathway. J. Pharm. Sci. 98, 3499-3508.

(52) Anthony, R. M., and Ravetch, J. V. (2010) A novel role for the IgG Fc glycan: the anti-inflammatory activity of sialylated IgG Fcs. J. Clin. Immunol. 30 (Suppl 1), S9-14.

(53) Yu, H., Chokhawala, H., Karpel, R., Yu, H., Wu, B., Zhang, J., Zhang, Y., Jia, Q., and Chen, X. (2005) A multifunctional Pasteurella multocida sialyltransferase: a powerful tool for the synthesis of sialoside libraries. J. Am. Chem. Soc. 127, 17618-17619.

(54) Yu, H., Huang, S., Chokhawala, H., Sun, M., Zheng, H., and Chen, X. (2006) Highly efficient chemoenzymatic synthesis of naturally occurring and non-natural α-2,6-linked sialosides: AP. damsela α-2,6-sialyltransferase with extremely flexible donor-substrate specificity. Angew. Chem., Int. Ed. 45, 3938-3944.

(55) Khedri, Z., Muthana, M. M., Li, Y., Muthana, S. M., Yu, H., Cao, H., and Chen, X. (2012) Probe sialidase substrate specificity using chemoenzymatically synthesized sialosides containing C9-modified sialic acid. Chem. Commun. 48, 3357-3359.

(56) Cane, D. E., Walsh, C. T., and Khosla, C. (1998) Harnessing the biosynthetic code: combinations, permutations, and mutations. Science 282, 63-68.

(57) Marahiel, M. A., Stachelhaus, T., and Mootz, H. D. (1997) Modular peptide synthetases involved in nonribosomal peptide synthesis. Chem. Rev. 97, 2651-2674.

(58) Staunton, J., and Weissman, K. J. (2001) Polyketide biosyn-thesis: a millennium review. Nat. Prod. Rep. 18, 380-416.

(59) Wakil, S. J., Stoops, J. K., and Joshi, V. C. (1983) Fatty acid synthesis and its regulation. Annu. Rev. Biochem. 52, 537-579.

(60) Walsh, C. T., Gehring, A. M., Weinreb, P. H., Quadri, L. E., and Flugel, R. S.

(1997) Post-translational modification of polyketide and nonribosomal peptide synthases. Curr. Opin. Chem. Biol. 1, 309-315.

(61) Yin, J., Liu, F., Li, X., and Walsh, C. T. (2004) Labeling proteins with small molecules by site-specific posttranslational modification. J. Am. Chem. Soc. 126, 7754-7755.

(62) Zhou, Z., Cironi, P., Lin, A. J., Xu, Y., Hrvatin, S., Golan, D. E., Silver, P. A., Walsh, C. T., and Yin, J. (2007) Genetically encoded short peptide tags for orthogonal protein labeling by Sfp and AcpS phosphopantetheinyl transferases. ACS Chem. Biol. 2, 337-346.

(63) Clarke, K. M., Mercer, A. C., La Clair, J. J., and Burkart, M. D. (2005) In vivo reporter labeling of proteins via metabolic delivery of coenzyme A analogues. J. Am. Chem. Soc. 127, 11234-11235.

(64) Worthington, A. S., and Burkart, M. D. (2006) One-pot chemo-enzymatic synthesis of reporter-modified proteins. Org. Biomol. Chem. 4, 44.

(65) Kosa, N. M., Haushalter, R. W., Smith, A. R., and Burkart, M. D. (2012) Reversible labeling of native and fusion-protein motifs. Nat. Methods 9, 981-984.

(66) George, N., Pick, H., Vogel, H., Johnsson, N., and Johnsson, K. (2004) Specific labeling of cell surface proteins with chemically diverse compounds. J. Am. Chem. Soc. 126, 8896-8897.

(67) Cappellaro, C., Baldermann, C., Rachel, R., and Tanner, W. (1994) Mating type-specific cell-cell recognition of Saccharomyces cerevisiae: cell wall attachment and active sites of a- and alpha-agglutinin. EMBO J. 13, 4737-4744.

(68) Yin, J., Straight, P. D., McLoughlin, S. M., Zhou, Z., Lin, A. J., Golan, D. E., Kelleher, N. L., Kolter, R., and Walsh, C. T. (2005) Genetically encoded short peptide tag for versatile protein labeling by Sfp phosphopantetheinyl transferase. Proc. Natl. Acad. Sci. U.S.A. 102, 15815-15820.

(69) Wong, L. S., Thirlway, J., and Micklefield, J. (2008) Direct site-selective covalent protein immobilization catalyzed by a phospho-pantetheinyl transferase. J. Am. Chem. Soc. 130, 12456-12464.

(70) Vocadlo, D. J., Hang, H. C., Kim, E., Hanover, J. A., and Bertozzi, C. R. (2003) A chemical approach for identifying O-GlcNAc-modified proteins in cells. Proc. Natl. Acad. Sci. U.S.A. 100, 9116-9121.

(71) Saxon, E., and Bertozzi, C. R. (2000) Cell surface engineering by a modified Staudinger reaction. Science 287, 2007-2010.

(72) Khidekel, N., Arndt, S., Lamarre-Vincent, N., Lippert, A., Poulin-Kerstien, K. G., Ramakrishnan, B., Qasba, P. K., and Hsieh-Wilson, L. C. (2003) A chemoenzymatic approach toward the rapid and sensitive detection of O-GlcNAc posttranslational modifications. J. Am. Chem. Soc. 125, 16162-16163.

(73) Clark, P. M., Dweck, J. F., Mason, D. E., Hart, C. R., Buck, S. B., Peters, E. C., Agnew, B. J., and Hsieh-Wilson, L. C. (2008) Direct in-gel fluorescence detection and cellular imaging of O-GlcNAc-modified proteins. J. Am. Chem. Soc. 130, 11576-11577.

(74) Khidekel, N., Ficarro, S. B., Peters, E. C., and Hsieh-Wilson, L. C. (2004) Exploring the O-GlcNAc proteome: Direct identification of O-GlcNAc-modified proteins from the brain. Proc. Natl. Acad. Sci. U.S.A. 101, 13132-13137.

(75) Khidekel, N., Ficarro, S. B., Clark, P. M., Bryan, M. C., Swaney, D. L., Rexach, J. E., Sun, Y. E., Coon, J. J., Peters, E. C., and Hsieh-Wilson, L. C. (2007) Probing the dynamics of O-GlcNAc glycosylation in the brain using quantitative proteomics. Nat. Chem. Biol. 3, 339-348.

(76) Mazmanian, S. K., Liu, G., Ton-That, H., and Schneewind, 0. (1999) Staphylococcus aureus sortase, an enzyme that anchors surface proteins to the cell wall. Science 285, 760-763.

(77) Tsukiji, S., and Nagamune, T. (2009) Sortase-mediated ligation: a gift from gram-positive bacteria to protein engineering. Chem-BioChem 10, 787-798.

(78) Popp, M. W., Antos, J. M., Grotenbreg, G. M., Spooner, E., and Ploegh, H. L. (2007) Sortagging: a versatile method for protein labeling. Nat. Chem. Biol. 3, 707-708.

(79) Tanaka, T., Yamamoto, T., Tsukiji, S., and Nagamune, T. (2008) Site-specific protein modification on living cells catalyzed by sortase. ChemBioChem 9, 802-807.

(80) Strijbis, K., Spooner, E., and Ploegh, H. L. (2012) Protein ligation in living cells using sortase. Traffic 13, 780-789.

(81) Mohlmann, S., Mahlert, C., Greven, S., Scholz, P., and Harrenga, A. (2011) In vitro sortagging of an antibody Fab fragment: overcoming unproductive reactions of sortase with water and lysine side chains. ChemBioChem 12, 1774-1780.

(82) Popp, M. W., Dougan, S. K., Chuang, T.-Y., Spooner, E., and Ploegh, H. L. (2011) Sortase-catalyzed transformations that improve the properties of cytokines. Proc. Natl. Acad. Sci. U.S.A. 108, 3169-3174.

(83) Antos, J. M., Miller, G. M., Grotenbreg, G. M., and Ploegh, H. L. (2008) Lipid modification of proteins through sortase-catalyzed transpeptidation. J. Am. Chem. Soc. 130, 16338-16343.

(84) Guo, X., Wang, Q., Swarts, B. M., and Guo, Z. (2009) Sortase-catalyzed peptide-glycosylphosphatidylinositol analogue ligation. J. Am. Chem. Soc. 131, 9878-9879.

(85) Wu, Z., Guo, X., and Guo, Z. (2011) Sortase A-catalyzed peptide cyclization for the synthesis of macrocyclic peptides and glycopeptides. Chem. Commun. 47, 9218.

(86) Sinisi, A., Popp, M. W.-L., Antos, J. M., Pansegrau, W., Savino, S., Nissum, M., Rappuoli, R., Ploegh, H. L., and Buti, L. (2012) Development of an influenza virus protein array using sortagging technology. Bioconjugate Chem. 23, 1119-1126.

(87) Witte, M. D., Cragnolini, J. J., Dougan, S. K., Yoder, N. C., Popp, M. W., and Ploegh, H. L. (2012) Preparation of unnatural N-to-N and C-to-C protein fusions. Proc. Natl. Acad. Sci. U.S.A. 109, 11993-11998.

(88) Williamson, D. J., Fascione, M. A., Webb, M. E., and Turnbull, W. B. (2012) Efficient N-terminal labeling of proteins by use of sortase. Angew. Chem., Int. Ed. 124, 9511-9514.

(89) Claessen, J. H. L., Witte, M. D., Yoder, N. C., Zhu, A. Y., Spooner, E., and Ploegh, H. L. (2013) Catch-and-release probes applied to semi-intact cells reveal ubiquitin-specific protease expression in Chlamydia trachomatis infection. ChemBioChem 14, 343-352.

(90) Jeger, S., Zimmermann, K., Blanc, A., Grunberg, J., Honer, M., Hunziker, P., Struthers, H., and Schibli, R. (2010) Site-specific and stoichiometric modification of antibodies by bacterial transglutaminase. Angew. Chem., Int. Ed. 49, 9995-9997.

(91) Mero, A., Spolaore, B., Veronese, F. M., and Fontana, A. (2009) Transglutaminase-mediated PEGylation of proteins: direct identification of the sites of protein modification by mass spectrometry using a novel monodisperse PEG. Bioconjugate Chem. 20, 384-389.

(92) Abe, H., Goto, M., and Kamiya, N. (2011) Protein lipidation catalyzed by microbial transglutaminase. Chem. • Eur. J. 17, 14004-14008.

(93) Tanaka, T., Kamiya, N., and Nagamune, T. (2005) N-terminal glycine-specific protein conjugation catalyzed by microbial trans-glutaminase. FEBS Lett. 579, 2092-2096.

(94) Tominaga, J., Kamiya, N., Doi, S., Ichinose, H., Maruyama, T., and Goto, M. (2005) Design of a specific peptide tag that affords covalent and site-specific enzyme immobilization catalyzed by microbial transglutaminase. Biomacromolecules 6, 2299-2304.

(95) Lin, C.-W., and Ting, A. Y. (2006) Transglutaminase-catalyzed site-specific conjugation of small-molecule probes to proteins in vitro and on the surface of living cells. J. Am. Chem. Soc. 128, 4542-4543.

(96) Duckworth, B. P., Xu, J., Taton, T. A., Guo, A., and Distefano, M. D. (2006) Site-specific, covalent attachment of proteins to a solid surface. Bioconjugate Chem. 17, 967-974.

(97) Kho, Y. (2004) A tagging-via-substrate technology for detection and proteomics of farnesylated proteins. Proc. Natl. Acad. Sci. U.S.A. 101, 12479-12484.

(98) Duckworth, B. P., Zhang, Z., Hosokawa, A., and Distefano, M. D. (2007) Selective labeling of proteins by using protein farnesyltransferase. ChemBioChem 8, 98-105.

(99) Rashidian, M., Dozier, J. K., Lenevich, S., and Distefano, M. D. (2010) Selective labeling of polypeptides using protein farnesyl-transferase via rapid oxime ligation. Chem. Commun. 46, 8998-9000.

(100) Nguyen, U. T. T., Guo, Z., Delon, C., Wu, Y., Deraeve, C., Franzel, B., Bon, R. S., Blankenfeldt, W., Goody, R. S., Waldmann, H., Wolters, D., and Alexandrov, K. (2009) Analysis of the eukaryotic prenylome by isoprenoid affinity tagging. Nat. Chem. Biol. 5, 227-235.

(101) Subramanian, T., Pais, J. E., Liu, S., Troutman, J. M., Suzuki, Y., Leela Subramanian, K., Fierke, C. A., Andres, D. A., and Spielmann, H. P. (2012) Farnesyl diphosphate analogues with aryl moieties are efficient alternate substrates for protein farnesyltransferase. Biochem-istry 51, 8307-8319.

(102) Labadie, G. R., Viswanathan, R., and Poulter, C. D. (2007) Farnesyl diphosphate analogues with ω-bioorthogonal azide and alkyne functional groups for protein farnesyl transferase-catalyzed ligation reactions. J. Org. Chem. 72, 9291-9297.

(103) Weinrich, D., Lin, P.-C., Jonkheijm, P., Nguyen, U. T. T., Schroder, H., Niemeyer, C. M., Alexandrov, K., Goody, R., and Waldmann, H. (2010) Oriented immobilization of farnesylated proteins by the thiol-ene reaction. Angew. Chem., Int. Ed. 49, 1252-1257.

(104) Nguyen, U. T. T., Cramer, J., Gomis, J., Reents, R., Gutierrez-Rodriguez, M., Goody, R. S., Alexandrov, K., and Waldmann, H. (2007) Exploiting the substrate tolerance of farnesyltransferase for site-selective protein derivatization. ChemBioChem 8, 408-423.
(105) Rose, M. W., Xu, J., Kale, T. A., O'Doherty, G., Barany, G., and Distefano, M. D. (2005) Enzymatic incorporation of orthogonally reactive prenylazide groups into peptides using geranylazide diphosphate via protein farnesyltransferase: implications for selective protein labeling. Biopolymers 80, 164-171.
(106) Rose, M. W., Rose, N. D., Boggs, J., Lenevich, S., Xu, J., Barany, G., and Distefano, M. D. (2005) Evaluation of geranylazide and farnesylazide diphosphate for incorporation of prenylazides into a CAAX box-containing peptide using protein farnesyltransferase. J. Pept. Res. 65, 529-537.
(107) Xu, J., DeGraw, A. J., Duckworth, B. P., Lenevich, S., Tann, C.-M., Jenson, E. C., Gruber, S. J., Barany, G., and Distefano, M. D. (2006) Synthesis and reactivity of 6,7-dihydrogeranylazides: reagents for primary azide incorporation into peptides and subsequent Staudinger ligation. Chem. Biol. Drug. Des. 68, 85-96.
(108) Duckworth, B. P., Chen, Y., Wollack, J. W., Sham, Y., Mueller, J. D., Taton, T. A., and Distefano, M. D. (2007) A universal method for the preparation of covalent protein-DNA conjugates for use in creating protein nanostructures. Angew. Chem. 119, 8975-8978.
(109) Khatwani, S. L., Kang, J. S., Mullen, D. G., Hast, M. A., Beese, L. S., Distefano, M. D., and Taton, T. A. (2012) Covalent protein-oligonucleotide conjugates by copper-free click reaction. Bioorg. Med. Chem. 20, 4532-4539.
(110) Speers, A. E., and Cravatt, B. F. (2004) Profiling enzyme activities in vivo using click chemistry methods. Chem. Biol. 11, 535-546.
(111) Hosokawa, A., Wollack, J. W., Zhang, Z., Chen, L., Barany, G., and Distefano, M. D. (2007) Evaluation of an alkyne-containing analogue of farnesyl diphosphate as a dual substrate for protein-prenyltransferases. Int. J. Pept. Res. Ther. 13, 345-354.
(112) Wollack, J. W., Silverman, J. M., Petzold, C. J., Mougous, J. D., and Distefano, M. D. (2009) A minimalist substrate for enzymatic peptide and protein conjugation. ChemBioChem 10, 2934-2943.
(113) Mahmoodi, M. M., Rashidian, M., Dozier, J. K., and Distefano, M. D. (2013) Chemoenzymatic reversible immobilization and labeling of proteins from crude cellular extract. Curr. Protoc. Chem. Biol., 89-109.
(114) Dirksen, A., Hackeng, T. M., and Dawson, P. E. (2006) Nucleophilic catalysis of oxime ligation. Angew. Chem., Int. Ed. 45, 7581-7584.
(115) Rashidian, M., Mahmoodi, M. M., Shah, R., Dozier, J. K., Wagner, C. R., and Distefano, M. D. (2013) A highly efficient catalyst for oxime ligation and hydrazone-oxime exchange suitable for bioconjugation. Bioconjugate Chem. 24, 333-342.
(116) Crisalli, P., and Kool, E. T. (2013) Water-soluble organo-catalysts for hydrazone and oxime formation. J. Org. Chem. 78, 1184-1189.
(117) Algar, W. R., Prasuhn, D. E., Stewart, M. H., Jennings, T. L., Blanco-Canosa, J. B., Dawson, P. E., and Medintz, I. L. (2011) The controlled display of biomolecules on nanoparticles: a challenge suited to bioorthogonal chemistry. Bioconjugate Chem. 22, 825-858.
(118) Howarth, M., Takao, K., hayashi, Y., and Ting, A. Y. (2005) Targeting quantum dots to surface proteins in living cells with biotin ligase. Proc. Natl. Acad. Sci. U.S.A. 102, 7583-7588.
(119) Howarth, M., Liu, W., Puthenveetil, S., Zheng, Y., Marshall, L. F., Schmidt, M. M., Wittrup, K. D., Bawendi, M. G., and Ting, A. Y. (2008) Monovalent, reduced-size quantum dots for imaging receptors on living cells. Nat. Meth. 5, 397-399.
(120) Slavoff, S. A., Chen, I., Choi, Y.-A., and Ting, A. Y. (2008) Expanding the substrate tolerance of biotin ligase through exploration of enzymes from diverse species. J. Am. Chem. Soc. 130, 1160-1162.
(121) Fernandez-Suarez, M., Chen, T. S., and Ting, A. Y. (2008) Protein-protein interaction detection in vitro and in cells by proximity biotinylation. J. Am. Chem. Soc. 130, 9251-9253.
(122) Sueda, S., Yoneda, S., and Hayashi, H. (2011) Site-specific labeling of proteins by using biotin protein ligase conjugated with fluorophores. ChemBioChem 12, 1367-1375.
(123) Roux, K. J., Kim, D. I., Raida, M., and Burke, B. (2012) A promiscuous biotin ligase fusion protein identifies proximal and interacting proteins in mammalian cells. J. Cell Biol. 196, 801-810.
(124) Fernandez-Suarez, M., Baruah, H., Martinez-Hernandez, L., Xie, K. T., Baskin, J. M., Bertozzi, C. R., and Ting, A. Y. (2007) Redirecting lipoic acid ligase for cell surface protein labeling with small-molecule probes. Nat. Biotechnol. 25, 1483-1487.
(125) Cohen, J. D., Thompson, S., and Ting, A. Y. (2011) Structure-guided engineering of a pacific blue fluorophore ligase for specific protein imaging in living cells. Biochemistry 50, 8221-8225.
(126) Uttamapinant, C., White, K. A., Baruah, H., Thompson, S., Fernandez-Suarez, M., Puthenveetil, S., and Ting, A. Y. (2010) From the cover: a fluorophore ligase for site-specific protein labeling inside living cells. Proc. Natl. Acad. Sci. U.S.A. 107, 10914-10919.
(127) Slavoff, S. A., Liu, D. S., Cohen, J. D., and Ting, A. Y. (2011) Imaging protein-protein interactions inside living cells via interaction-dependent fluorophore ligation. J. Am. Chem. Soc. 133, 19769-19776.
(128) Cohen, J. D., Zou, P., and Ting, A. Y. (2012) Site-specific protein modification using lipoic acid ligase and bis-aryl hydrazone formation. ChemBioChem 13, 888-894.
(129) Uttamapinant, C., Tangpeerachaikul, A., Grecian, S., Clarke, S., Singh, U., Slade, P., Gee, K. R., and Ting, A. Y. (2012) Fast, cell-compatible click chemistry with copper-chelating azides for bio-molecular labeling. Angew. Chem., Int. Ed. 51, 5852-5856.
(130) Yao, J. Z., Uttamapinant, C., Poloukhtine, A., Baskin, J. M., Codelli, J. A., Sletten, E. M., Bertozzi, C. R., Popik, V. V., and Ting, A. Y. (2012) Fluorophore targeting to cellular proteins via enzyme-mediated azide ligation and strain-promoted cycloaddition. J. Am. Chem. Soc. 134, 3720-3728.
(131) Farazi, T. A., Waksman, G., and Gordon, J. I. (2001) The biology and enzymology of protein N-myristoylation. J. Biol. Chem. 276, 39501-39504.
(132) Towler, D. A., Gordon, J. I., Adams, S. P., and Glaser, L. (1988) The biology and enzymology of eukaryotic protein acylation. Annu. Rev. Biochem. 57, 69-99.
(133) Price, H. P., Menon, M. R., Panethymitaki, C., Goulding, D., McKean, P. G., and Smith, D. F. (2003) Myristoyl-CoA:protein N-myristoyltransferase, an essential enzyme and potential drug target in kinetoplastid parasites. J. Biol. Chem. 278, 7206-7214.
(134) Martinez, A., Traverso, J. A., Valot, B., Ferro, M., Espagne, C., Ephritikhine, G., Zivy, M., Giglione, C., and Meinnel, T. (2008) Extent of N-terminal modifications in cytosolic proteins from eukaryotes. Proteomics 8, 2809-2831.
(135) Wright, M. H., Heal, W. P., Mann, D. J., and Tate, E. W. (2010) Protein myristoylation in health and disease. J. Chem. Biol. 3, 19-35.
(136) Heal, W. P., Wickramasinghe, S. R., Bowyer, P. W., Holder, A. A., Smith, D. F., Leatherbarrow, R. J., and Tate, E. W. (2008) Site-specific N-terminal labelling of proteins in vitro and in vivo using N-myristoyl transferase and bioorthogonal ligation chemistry. Chem. Commun., 480.
(137) Heal, W. P., Wickramasinghe, S. R., Leatherbarrow, R. J., and Tate, E. W. (2008) N-Myristoyl transferase-mediated protein labelling in vivo. Org. Biomol. Chem. 6, 2308.
(138) Heal, W. P., Wright, M. H., Thinon, E., and Tate, E. W. (2012) Multifunctional protein labeling via enzymatic N-terminal tagging and elaboration by click chemistry. Nat. Protoc. 7, 105-117.

Definitions

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which the present disclosure belongs. As used herein the following terms have the following meanings.

As used herein, the term "about" when used before a numerical designation, e.g., temperature, time, amount, concentration, and such other, including a range, indicates approximations which may vary by (+) or (−) 10%, 5% or 1%.

As used herein, the term "administration" may be effected in one dose, continuously or intermittently or by several subdoses which in the aggregate provide for a single dose. Dosing can be conducted throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include intratumoral delivery, peritumoral delivery, intraperitoneal delivery, intrathecal delivery, intramuscular injection, subcutaneous injection, intravenous delivery, nasal spray and other mucosal delivery (e.g. transmucosal delivery), intra-arterial delivery, intraventricular delivery, intrasternal delivery, intracranial delivery, intradermal injection, electroincorporation (e.g., with electroporation), ultrasound, jet injector, oral and topical patches.

A "therapeutic agent," as used herein, may be a molecule, or compound that is useful in treatment of a disease or condition. A "therapeutically effective amount," "therapeutically effective concentration" or "therapeutically effective dose" is the amount of a compound that produces a desired therapeutic effect in a subject, such as preventing or treating a target condition, alleviating symptoms associated with the condition, producing a desired physiological effect, or allowing imaging or diagnosis of a condition that leads to treatment of the disease or condition. The precise therapeutically effective amount is the amount of the composition that will yield the most effective results in terms of efficacy of treatment in a given subject. This amount will vary depending upon a variety of factors, including, but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

As used herein, "in combination" or "in combination with," when used herein in the context of multiple agents, therapeutics, or treatments, means in the course of treating the same disease or condition in a subject administering two or more agents, drugs, treatment regimens, treatment modalities or a combination thereof. This includes simultaneous administration (or "coadministration"), administration of a first agent prior to or after administration of a second agent, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

"Treating" or "treatment" of a condition, disease or disorder may refer to preventing the condition, disease or disorder, slowing the onset or rate of development of the condition, disease or disorder, reducing the risk of developing the condition, disease or disorder, preventing or delaying the development of symptoms associated with the condition, disease or disorder, reducing or ending symptoms associated with the condition, disease or disorder, generating a complete or partial regression of the condition, disease or disorder, or some combination thereof. Examples of neoplastic diseases or disorders include colorectal cancer, osteosarcoma, non-small cell lung cancer, breast cancer, ovarian cancer, glial cancer, solid tumors, metastatic tumor, acute lymphoblastic leukemia, acute myelogenous leukemia, adrenocortical carcinoma, Kaposi sarcoma, lymphoma, anal cancer, astrocytomas, basal cell carcinoma, bile duct cancer, bladder cancer, bone cancer, brain tumor, breast cancer, bronchial tumor, cervical cancer, chronic lymphocytic leukemia, chronic myelogenous leukemia, chronic myeloproliferative disorders, colon cancer, colorectal cancers, ductal carcinoma in situ, endometrial cancer, esophageal cancer, eye cancer, intraocular, retinoblastoma, metastatic melanoma, gallbladder cancer, gastric cancer, gastrointestinal carcinoid tumor, gastrointestinal stromal tumors, glioblastoma, glioma, hairy cell leukemia, head and neck cancer, hepatocellular carcinoma, hepatoma, Hodgkin lymphoma, hypopharyngeal cancer, Langerhans cell histiocytosis, laryngeal cancer, lip and oral cavity cancer, liver cancer, lobular carcinoma in situ, lung cancer, non-small cell lung cancer, small cell lung cancer, lymphoma, AIDS-related lymphoma, Burkitt lymphoma, non-Hodgkin lymphoma, cutaneous T-cell lymphoma, melanoma, squamous neck cancer, mouth cancer, multiple myeloma, myelodysplastic syndromes, myelodysplastic/myeloproliferative neoplasms, nasal cavity and paranasal sinus cancer, nasopharyngeal cancer, neuroblastoma, oral cavity cancer, oropharyngeal cancer, osteosarcoma, ovarian cancer, pancreatic carcinoma, papillary carcinomas, parathyroid cancer, penile cancer, pharyngeal cancer, pheochromocytoma, pineal parenchymal tumors, pineoblastoma, pituitary tumor, pleuropulmonary blastoma, primary central nervous system lymphoma, prostate cancer, rectal cancer, renal cell cancer, salivary gland cancer, sarcoma, Ewing sarcoma, soft tissue sarcoma, squamous cell carcinoma, Sezary syndrome, skin cancer, Merkel cell carcinoma, testicular cancer, throat cancer, thymoma, thymic carcinoma, thyroid cancer, urethral cancer, endometrial cancer, uterine cancer, uterine sarcoma, vaginal cancer, vulvar cancer, Waldenstrom macroglobulinemia, and Wilms tumor.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein. Tumor or cancer status may also be assessed by sampling for the number, concentration or density of tumor or cancer cells, alone or with respect to a reference. In accordance with the practice of the invention, inhibiting a tumor may be measured in any way as is known and accepted in the art, including complete regression of the tumor(s) (complete response); reduction in size or volume of the tumor(s) or even a slowing in a previously observed growth of a tumor(s), e.g., at least about a 10-30% decrease in the sum of the longest diameter (LD) of a tumor, taking as reference the baseline sum LD (partial response); mixed response (regression or stabilization of some tumors but not others); or no apparent growth or progression of tumor(s) or neither sufficient shrinkage to qualify for partial response nor sufficient increase to qualify for progressive disease, taking as reference the smallest sum LD since the treatment started (stable disease).

"Polynucleotide," or "nucleic acid," as used interchangeably herein, refer to polymers of nucleotides of any length, and include DNA and RNA. "oligonucleotide" refers to a nucleotide having a chain length of less than 250 nucleotides. The nucleotides can be deoxyribonucleotides, ribonucleotides, modified nucleotides, and/or their analogs, including epigenetically modified variants, or any substrate that can be incorporated into a polymer by DNA or RNA polymerase, or by a synthetic reaction.

A "subject" is a vertebrate, preferably a mammal, more preferably a human. Mammals include, but are not limited to, farm animals (such as cows), pets (such as cats, dogs and horses), primates, mice and rats.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

According to the present invention, where administration includes a pharmaceutical formulation, preferably the formulation is a unit dosage containing a daily dose or unit, daily sub-dose or an appropriate fraction thereof, of the active ingredient (also referred to herein as a therapeutic agent).

The compositions of the invention can be administered by any parenteral route, in the form of a pharmaceutical formulation comprising the active ingredient, optionally in the form of a nontoxic organic, or inorganic, acid, or base, addition salt, in a pharmaceutically acceptable dosage form. Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

In embodiments of the present invention in which polypeptides or polynucleotides of the invention are administered parenterally, such administration can be, for example, intravenously, intra-arterially, intraperitoneally, intrathecally, intraventricularly, intracisternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Therapeutic formulations may be prepared for storage by mixing an active component having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes. When appropriate, chemical or radiation sterilization method may be used.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma.-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37 C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. The formulation may also be an immediate-release formulation. The formation may also be a combination of an immediate-release formulation and a sustained-release formulation.

The medicaments and/or pharmaceutical compositions may be present in a unit dosage containing a daily dose or unit, daily sub-dose or an appropriate fraction thereof, of the active ingredient.

The agents, medicaments and pharmaceutical compositions of the invention may be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the agents, medicaments and pharmaceutical compositions of the invention can be administered orally, buccally or sublingually in the form of tablets, capsules, ovules, elixirs, solutions or suspensions, which may contain flavoring or coloring agents, for immediate-, delayed- or controlled-release applications. Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents, medicaments and pharmaceutical compositions of the invention may be combined with various sweetening or flavoring agents, coloring matter or dyes, with emulsifying and/or suspending agents and with diluents such as water, ethanol, propylene glycol and glycerin, and combinations thereof.

The agents, medicaments and pharmaceutical compositions can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art. Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the agents, medicaments and pharmaceutical compositions of the invention will usually be from 10 μg to 500 mg per adult per day administered in single or divided doses.

The agents, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an agent of the invention and a suitable powder base such as lactose or starch.

Aerosol or dry powder formulations are preferably arranged so that each metered dose or "puff" contains at least 1 mg of an agent of the invention for delivery to the patient. It will be appreciated that he overall daily dose with an aerosol will vary from patient to patient, and may be administered in a single dose or, more usually, in divided doses throughout the day.

Alternatively, the agents, medicaments and pharmaceutical compositions can be administered in the form of a suppository or pessary, or they may be applied topically in the form of a lotion, solution, cream, gel, ointment or dusting powder. The agents, medicaments and pharmaceutical compositions of the invention may also be transdermally administered, for example, by the use of a skin patch, ointment, cream or lotion. For application topically to the skin, the agents, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

They may also be administered by the ocular route, particularly for treating diseases of the eye. For ophthalmic use, the agents, medicaments and pharmaceutical compositions can be formulated as soluble suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Agents may be formulated at various concentrations, depending on the efficacy/toxicity of the compound being used, for example as described in the accompanying Examples. For in vitro applications, formulations may comprise a lower concentration of a compound of the invention.

Pharmaceutically acceptable base addition salts may also be used to produce pharmaceutically acceptable salt forms of the agents.

The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

SUMMARY OF THE INVENTION

Autoproteolytic cleavage is a critical step in the maturation of Hedgehog (Hh) proteins, where a precursor form of Hh is activated for nucleophilic attack by cholesterol. No cofactors, energy source or accessory proteins are required for this unusual cholesterolysis event; instead, all catalytic activity resides in a ~26 kDa segment of the Hh precursor. This autocatalytic element, termed hedgehog steroyl transferase I (HST-I) or hedgehog terminal transferase (HT-Tase), or HhC, may be used as a tool for protein labeling. HST-I is modular; and its activity is retained when fused to the C-terminus of heterologous peptides and proteins.

Using an optical assay developed to monitor HST-I, heterologous proteins can be covalently modified at their C-terminus by cholesterol with a $t_{1/2}$ of 10-20 min at pH 7.1, 25 degrees Celsius. During the reaction, HST-I is liberated from the heterologous protein, rendering the reaction "traceless", i.e., the product does not contain required traces of the HST-I component.

Sterols other than cholesterol may be used as substrates. In addition to cholesterol, HST-I will also ligate proteins to sterol derivatives equipped with fluorescent reporters, alkynes, and biotin, among other functional groups.

Typically, cholesterol modified proteins partition to eukaryotic cell membranes.

See, (139) Cholesterol modification of hedgehog signaling proteins in animal development. Porter J A, Young K E, Beachy P A. Science. 1996 274. 255-9.

(140) Targeting of proteins to membranes through hedgehog auto-processing. Vincent S, Thomas A, Brasher B, Benson J D. Nat Biotechnol. 2003 21:936-40.

(141) Enzymatic labeling of proteins: techniques and approaches. Rashidian M, Dozier J K, Distefano M D. Bioconjug Chem. 2013 24:1277-94.

Hedgehog terminal transferase (HST-I) thus provides a tool which can be used to covalently conjugate virtually any protein with a variety of small molecules, from fluorophores to therapeutics. HST-I is a water soluble protein that catalyzes protein conjugation in <60 min in the absence accessory proteins.

Features of protein-conjugation with HST-I include: (1) two-component labeling kinetics (2) site-specific, stoichiometric modification (3) broad substrate tolerance and (4) labeling that is nearly traceless. The last feature is particularly noteworthy as existing protein conjugation methods require addition to the target protein of anywhere from 4 to 296 amino acids. That residual sequence can compromise function or engender an immune response during therapeutic application. Conjugation with HST-I requires addition to the target protein of a single glycine residue only (unless it is already present and available).

A general approach is provided for biocatalytic protein-small molecule conjugation, where the reaction is site-specific (C-terminus), stoichiometric (1:1), and nearly traceless (1 or 2 amino acid "scar"). The catalyst for this reaction, called HST-I, has the amino acid sequence (from *Drosophila melanogaster*), as follows:

```
                                    SEQ ID NO.: 001
G^CFTPESTALLESGVRKPLGELSIGDRVLSMTANGQAVYSEVILFMDRN

LEQMQNFVQLHTDGGAVLTVTPAHLVSVWQPESQKLTFVFADRIEEKNQV

LVRDVETGELRPQRVVKVGSVRSKGVVAPLTREGTIVVNSVAASCYAVIN

SQSLAHWGLAPMRLLSTLEAWLPAKEQLHSSPKVVSSAQQQNGIHWYANA

LYKVKDYVLPQSWRHD
```

The Hedgehog sterol transferase (HST-I) from *Drosophila melanogaster* HST-I conjugates the first amino acid (glycine, GA) to a sterol through a carboxylic acid ester. Other steroyl transferases and/or hedgehog terminal transferases with homology to HST-I may also be used, in similar fashion (For related sequences see: Bürglin, Thomas R. "The Hedgehog protein family." Genome biology 9, no. 11 (2008): 241, www.ncbi.nlm.nih.gov/pubmed/19040769). Homologous proteins are endogenous to multicellular organisms, vertebrates and invertebrates.

The native function of HST-I is to covalently couple the carboxyl terminus of a specific protein (substrate A) to cholesterol (substrate B). HST-I exhibits broad substrate tolerance toward substrate A and toward substrate B. Thus, proteins with no homology to the native protein substrate (substrate A) can be modified at their carboxyl terminus by HST-I; in addition, sterols other than cholesterol (substrate B), derivatized with a variety of functional groups can serve as the substrate for HST-I.

In each of these cases, the core steroid nucleus serves as the generic "linker" recognized by HST-I that ultimately joins protein to functional group.

A genetically engineered HST-I or HST-I derivative may be used, whose conjugation activity can be regulated by an exogenous trigger (redox, light); exhibits different solution properties (e.g., higher thermal stability; greater aggregation resistance); as well as HST-I derivatives that have been engineered to accept synthetic sterols with alterations to the fused ring system of sterols. The HST-I may also be switched, such as by pH, ligand or ionic binding, or the like.

HST-I has utility, particularly in the application areas of protein therapeutics (e.g. antibody-drug conjugates/protein-nucleic acid conjugates), protein detection, and protein immobilization. As one example, HST-I could be used to attach a therapeutic compound, or an imaging agent, to the caboxyl terminus of an antibody so as to target that cargo to a cancer cell bearing the appropriate antigen/receptor. In another embodiment, HST-I could be used to attach polypeptides to nanoparticles for biological or biophysical studies. HST-I can also be used to create protein-nucleic acids conjugates to enhance cellular delivery of therapeutic RNA or natural or synthetic polynucleotides.

Some examples include antibody-drug conjugates; protein-fluorophore labeling for imaging; protein immobilization for diagnostic applications (sensors); membrane-targeted therapeutics (hormones/antibacterials/inhibitors of membrane-bound enzymes); and membrane-targeted protein probes (GFP, etc.).

There are similarities and key distinctions of HST-I compared with other biocatalysts for protein conjugation. Conjugation by HST-I is residue specific; it is active in physiological buffer at room temperature; the kinetics are relatively fast (half time ~1 h or less); and a variety of protein substrates (substrate A) can be labeled with a broad range of small molecules (substrate B).

The application of HST-I generally correspond to the applications of Sortase enzyme and farnesyl transferase. See, U.S. Pat. Nos. 6,544,772; 6,620,585; 6,773,706; 6,790,448; 6,838,239; 6,841,154; 6,896,887; 6,908,994; 6,936,252; 6,994,982; 7,067,248; 7,067,621; 7,067,639; 7,101,692; 7,125,698; 7,179,458; 7,183,101; 7,195,763; 7,238,489; 7,270,969; 7,312,076; 7,348,420; 7,371,719; 7,384,775; 7,390,526; 7,452,679; 7,455,992; 7,456,011; 7,485,710; 7,491,690; 7,534,761; 7,534,876; 7,538,209; 7,541,039; 7,544,661; 7,554,021; 7,615,616; 7,632,515; 7,635,487; 7,648,708; 7,683,025; 7,709,009; 7,713,534; 7,722,888; 7,731,978; 7,745,708; 7,754,467; 7,763,420; 7,771,728; 7,771,731; 7,776,553; 7,776,589; 7,785,608; 7,803,765; 7,820,184; 7,829,681; 7,833,791; 7,838,010; 7,838,491; 7,850,974; 7,851,445; 7,858,357; 7,888,075; 7,897,367; 7,927,864; 7,935,804; 7,939,087; 7,955,604; 7,960,505; 7,960,533; 7,968,100; 7,968,297; 7,968,683; 8,007,803; 8,007,811; 8,025,885; 8,025,890; 8,038,990; 8,039,005; 8,063,014; 8,076,295; 8,088,611; 8,101,194; 8,105,612; 8,110,199; 8,124,107; 8,124,583; 8,128,936; 8,137,673; 8,138,140; 8,148,321; 8,241,642; 8,252,546; 8,263,642; 8,280,643; 8,287,885; 8,318,908; 8,323,660; 8,329,195; 8,372,411; 8,377,446; 8,399,651; 8,409,589; 8,431,139; 8,445,426; 8,450,271; 8,475,809; 8,524,241; 8,529,913; 8,557,961; 8,563,001; 8,563,006; 8,563,007; 8,568,735; 8,574,597; 8,575,070; 8,580,923; 8,580,939; 8,591,899; 8,592,375; 8,598,342; 8,609,106; 8,617,556; 8,632,783; 8,647,835; 8,652,800; 8,663,631; 8,663,926; 8,669,226; 8,673,860; 8,679,505; 8,680,050; 8,703,717; 8,709,431; 8,709,436; 8,709,760; 8,710,188; 8,715,688; 8,716,448; 8,722,354; 8,748,122; 8,754,198; 8,758,765; 8,772,049; 8,778,358; 8,795,965; 8,795,983; 8,808,699; 8,821,894; 8,822,409; 8,835,187; 8,835,188; 8,840,906; 8,841,249; 8,853,382; 8,858,957; 8,859,492; 8,865,479; 8,871,204; 8,871,445; 8,883,788; 8,889,145; 8,889,150; 8,889,356; 8,927,230; 8,932,814; 8,933,193; 8,933,197; 8,937,167; 8,940,501; 8,945,542; 8,945,588; 8,945,589; 8,945,855; 8,946,381; 8,957,021; 8,961,979; 8,975,232; 8,980,284; 8,980,824; 8,986,710; 8,993,295; 9,005,579; 9,050,374; 9,056,912; 9,062,299; 9,068,985; 9,079,946; 9,079,952; 9,080,159; 9,090,677; 9,095,540; 9,102,741; 9,107,873; 9,109,008; 9,114,105; 9,127,050; 9,128,058; 9,129, 785; 9,132,179; 9,132,182; 9,134,304; 9,150,626; 9,156,850; 9,168,293; 9,168,312; 9,181,297; 9,181,329; 9,182,390; 9,205,142; 9,212,219; 9,217,157; 9,221,882; 9,221,886; 9,221,902; 9,234,012; 9,238,010; 9,243,038; 9,249,211; 9,266,925; 9,266,943; 9,266,944; 9,267,127; 9,315,554; 9,340,582; 9,340,584; 9,353,160; 9,371,369; 9,376,672; 9,382,289; 9,388,225; 9,393,294; 9,394,092; 9,399,673; 9,403,904; 9,404,922; 9,405,069; 9,408,890; 9,409,952; 9,416,171; 9,434,774; 9,441,016; 9,458,228; 9,458,229; 9,463,431; 20020028457; 20030021789; 20030022178; 20030087864; 20030091577; 20030099940; 20030153020; 20030180816; 20030185833; 20030186851; 20030228297; 20040091856; 20040101919; 20040110181; 20040126870; 20040167068; 20040230033; 20040236072; 20050002925; 20050003510; 20050037444; 20050048545; 20050069984; 20050106648; 20050112612; 20050175581; 20050203280; 20050207995; 20050220788; 20050233396; 20050276814; 20060073530; 20060074016; 20060078901; 20060115491; 20060135416; 20060165716; 20060177462; 20060188975; 20060194226; 20060198852; 20060234222; 20060246080; 20060257413; 20060263846; 20060269538; 20060275315; 20070003667; 20070026011; 20070031832; 20070053924; 20070059295; 20070082006; 20070082007; 20070082866; 20070117197; 20070128210; 20070128211; 20070128229; 20070172495; 20070190029; 20070190063; 20070207170; 20070207171; 20070218075; 20070248581; 20070253964; 20070258955; 20070286866; 20080031877; 20080038287; 20080050361; 20080064079; 20080089899; 20080171059; 20080175857; 20080220441; 20080248522; 20080254070; 20080260768; 20090022753; 20090035780; 20090041744; 20090075839; 20090088337; 20090088372; 20090092582; 20090117113; 20090130115; 20090148408; 20090155304; 20090176967; 20090202578; 20090202593; 20090214476; 20090214537; 20090214584; 20090239264; 20090297548; 20090297549; 20090305252; 20090317420; 20090317421; 20100004324; 20100009917; 20100055761; 20100064393; 20100068220; 20100074923; 20100098789; 20100105865; 20100119534; 20100150943; 20100152054; 20100183614; 20100184624; 20100196524; 20100221288; 20100227341; 20100239554; 20100247561; 20100255026; 20100256070; 20100260706; 20100260790; 20100267053; 20100278740; 20100279328; 20100297183; 20100303864; 20100323956; 20110020323; 20110020385; 20110020420; 20110020900; 20110046008; 20110046060; 20110046061; 20110076299; 20110077199; 20110091956; 20110097360; 20110104168; 20110110982; 20110124520; 20110129935; 20110150918; 20110151053; 20110172146; 20110177976; 20110183863; 20110189187; 20110189236; 20110189664; 20110206616; 20110206676; 20110206692; 20110243976; 20110243977; 20110245480; 20110262477; 20110263501; 20110275132; 20110281745; 20110281764; 20110288005; 20110311536; 20110312881; 20110318339; 20110321183; 20120015379; 20120034261; 20120058906; 20120064103; 20120064104; 20120076814; 20120083599; 20120093840; 20120093850; 20120100174; 20120100569; 20120107340; 20120114686; 20120121643; 20120122123; 20120142682; 20120149590; 20120149710; 20120157665; 20120171211; 20120172303; 20120178691; 20120189649; 20120201844; 20120207778; 20120237536; 20120244189; 20120251568; 20120263701; 20120263703; 20120270797; 20120282247; 20120282289; 20120282670; 20120282700; 20120289454; 20120294880; 20120301428; 20120301433; 20120301496; 20120308595; 20120309679; 20120309701; 20120316071; 20130011386; 20130011428; 20130017997; 20130034575; 20130034847; 20130039884; 20130045211; 20130064845; 20130071416; 20130072420; 20130084648; 20130089525; 20130101665; 20130122043; 20130136746; 20130136761; 20130143955; 20130157281; 20130165389; 20130171183; 20130177940; 20130184177; 20130189287; 20130209494; 20130216568; 20130217592; 20130217612; 20130230550; 20130236419; 20130243818; 20130253175; 20130259889; 20130260404; 20130261293; 20130288266; 20130288267; 20130289251; 20130289253; 20130296257; 20130316946; 20130323819; 20130330335; 20130338030; 20130338047; 20130344010; 20140004138; 20140011709; 20140017764; 20140030697; 20140037650; 20140037669; 20140051834; 20140057317; 20140065171; 20140073639; 20140105818; 20140113832; 20140128289; 20140147873; 20140154286; 20140154287; 20140155319; 20140161915; 20140162949; 20140170702; 20140178425; 20140179006; 20140186265; 20140186327; 20140186350; 20140186354; 20140186358; 20140189896; 20140193438; 20140206840; 20140213515; 20140227295; 20140227298; 20140234972; 20140235828; 20140243280; 20140248702; 20140249296; 20140255470; 20140273231; 20140287509; 20140301974; 20140302084; 20140308318; 20140310830; 20140315314; 20140328819; 20140329706; 20140329750; 20140335095; 20140348868; 20140371136; 20140377289; 20150004155; 20150005233; 20150005481; 20150010566; 20150023879; 20150023959; 20150030594; 20150031134; 20150031563; 20150031604; 20150037359; 20150037421; 20150037828; 20150038421; 20150045535; 20150050717; 20150051082; 20150056239; 20150056240; 20150071957; 20150079132; 20150079681; 20150086576; 20150087545; 20150093406; 20150093413; 20150104468; 20150118183; 20150118264; 20150132324; 20150132335; 20150132339; 20150139984; 20150152134; 20150158929; 20150165062; 20150166640; 20150168405; 20150174130; 20150182588; 20150184142; 20150185216; 20150197538; 20150197734; 20150203834; 20150210756; 20150216960; 20150231228; 20150232518; 20150232541; 20150232560; 20150232561; 20150241440; 20150246024; 20150253335; 20150258210; 20150259389; 20150259397; 20150259431; 20150266943; 20150273040; 20150273042; 20150274800; 20150284452; 20150284477; 20150290362; 20150291704; 20150305361; 20150306212; 20150306218; 20150309021; 20150315248; 20150320882; 20150329590; 20150335724; 20150338579; 20150343051; 20150344862; 20150346195; 20150368322; 20150374811; 20150376266; 20160000895; 20160002338; 20160002346; 20160002645; 20160018397; 20160022776; 20160022833; 20160025740; 20160032346; 20160038581; 20160040158; 20160041157; 20160045885; 20160052982; 20160068583; 20160068589; 20160068591; 20160069894; 20160073671; 20160074497; 20160074498; 20160082046; 20160090351; 20160090404; 20160097773; 20160102137; 20160102332; 20160102344; 20160108091; 20160114046; 20160115222; 20160115488; 20160115489; 20160122405; 20160122451; 20160122707; 20160123991; 20160129101; 20160130299; 20160136298; 20160137698; 20160137711; 20160137720; 20160146786; 20160146794; 20160158335; 20160166634; 20160168232; 20160175412; 20160175441; 20160178627; 20160184421; 20160185791; 20160185817; 20160185828; 20160193355; 20160194363; 20160194410; 20160194627; 20160199454; 20160199510; 20160200742; 20160206566; 20160208233; 20160213744; 20160220686; 20160222096; 20160230216; 20160244747; 20160244784; 20160251409; 20160257749; 20160257932; 20160264624; 20160271268; 20160279192; 20160279257; 20160280748; 20160282369; 20160287734; 20160297854; each of which is expressly incorporated herein by reference. Likewise, applications provided in U.S. 2015/0329568, expressly incorporated herein by reference in its entirety, may be employed as appropriate.

There are two key advantages of HST-I over sortase and farnestyl transferase biocatalysts for protein conjugation: First, HST-I allows a one-pot, bi-molecular conjugation, whereas existing sortase and farnesyl transferase bioconjugations require 3 component reactions. Second, the conjugation reaction with HST-I is nearly traceless, as the HST-I cleaves itself from the target protein during conjugation. The bi-molecular labelling (i) stems from the fact that the catalyst, HST-I, is fused to the protein substrate (substrate A), thus only the modifier (substrate B) needs to be added to the "pot" to initiate conjugation. No cofactors or accessory proteins are required.

Existing methods that require at least three separate components (the protein of interest; the small molecule; and the conjugation catalyst). Three component coupling reactions often proceed slowly, and require excess reactant concentration to drive conjugation to completion.

The traceless feature arises from the fact that the protein of interest is liberated from HST-I upon labelling. Existing chemical labeling methods require addition to the protein of anywhere from 4 to 296 amino acid residues to allow recognition by the conjugation catalyst. That residual "scar" may compromise stability, perturb protein-protein association, or engender an immune response, which would be a serious concern for therapeutic applications, in contrast to the single glycine residue required by HST-I.

Labeling is restricted to a protein's carboxyl terminus.

The sterol moiety that functions as the generic linker is typically hydrophobic, which could compromise solubility of the labeled protein if a water-soluble/hydrophilic product is required.

The technology does require fusion of the protein of interest to HST-I, which is typically performed by genetically engineering the protein of interest fused to the HST-I, though other mechanisms of ligation may be employed.

The catalytic activity of HST-I, i.e., Hedgehog sterol transferase (HST-I, 26 kDa) does not need the entire hedgehog protein, 46 kDa, but rather only the C-terminal portion of the hedgehog protein. A signaling protein, HhN, is in the adjacent N-terminal region of the hedgehog protein, is not required for catalytic activity.

The native function of HST-I in *Drosophila*, and in other multicellular organisms, is to conjugate cholesterol to the last residue of HhN, which is invariably glycine. The lipid becomes joined to the carboxyl group of glycine through an ester (www.ncbi.nlm.nih.gov/pubmed/8824192). Conjugation by HST-I releases the cholesterol-modified protein, thereby generating two polypeptides; HhN-cholesterol and HST-I.

In vitro HST-I exhibits broad substrate tolerance. For example, conjugation proceeds even when HST-I is translationally fused to heterologous proteins. Examples of heterologous proteins include fluorescent proteins, enzymes, carbohydrate binding proteins, and peptides. These proteins, with no homology to the native substrate polypeptide, HhN, undergo efficient conjugation at a C-terminal glycine residue catalyzed by HST-I. Derivatives of cholesterol modified with a variety of chemical matter, including oligonucleotides, serve as suitable substrates for HST-I. In these non-native conjugation events, the steroid appears to serves as a kind of "molecular handle" recognized by HST-I and ultimately activated by HST-I so as to react with the final residue of the heterologous protein.

Advantages of conjugation of a nucleic acid with a protein of interest (POI), using HST-1 and a steroylated nucleic acid include:

(i) labeling reactions that require two components (POI-HST-I fusion protein, steroylated DNA);

(ii) site-specific, stoichiometric modification at the C-terminus of the POI;

(iii) broad substrate tolerance; and (iv) labeling that is nearly traceless as HST-I is cleaved off from the POI concurrent with conjugation.

Example sterols and derivatized sterols include:

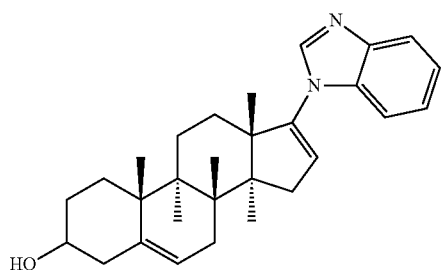

(1)

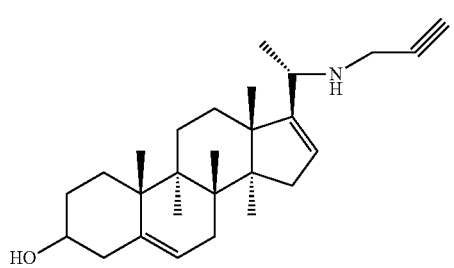

(2)

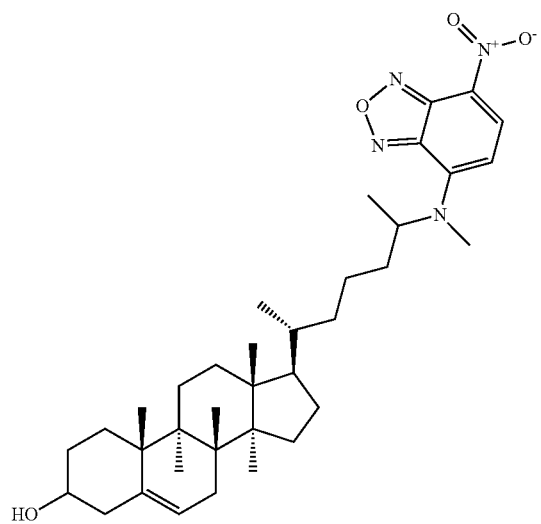
(3)
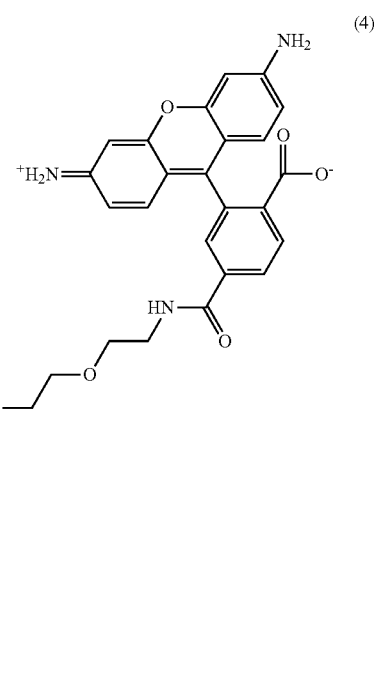
(4)

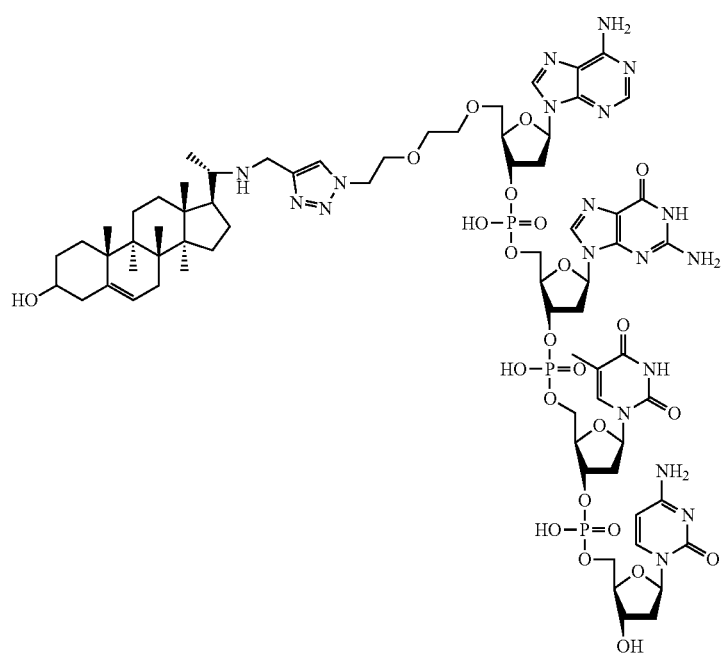
(5)
Formulas I and II are metal chelators, and Formulas III and IV are fluorophores. Formula V is a steroylated nucleic acid.
25 NBD-Chol:
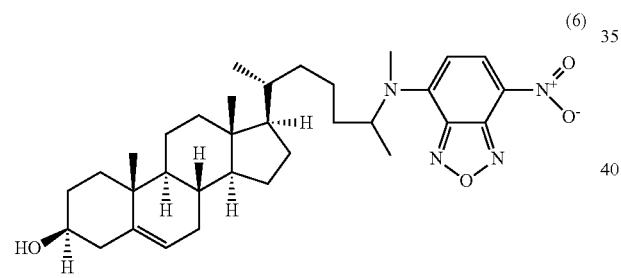
(6)
Sterol derivatives may be prepared, for example, through a process as follows:
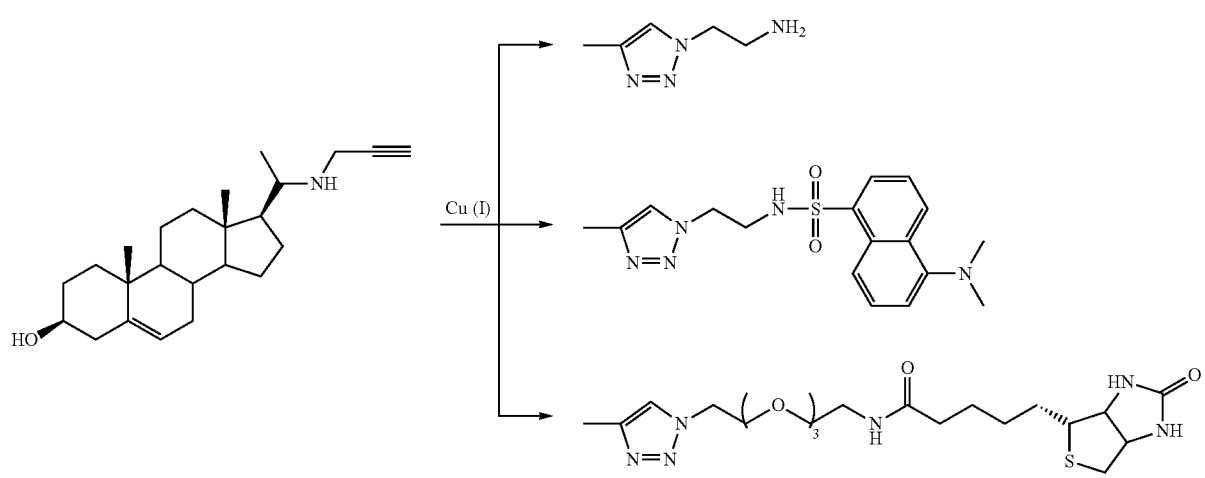
(2)

For example, derivatives may be prepared in one-pot by reductive amination of pregnenolone with propargylamine. Diastereomers are separable by silica gel chromatography.

It is therefore an object to provide a method comprising: providing a purified fusion protein comprising a C-terminal steroyl transferase activity from a hedgehog protein, an intervening electrophilic amino acid, and an N-terminal polypeptide; reacting the purified fusion protein with a substrate for the steroyl transferase activity comprising a fused sterol or stanol ring system having a nucleophilic substituent of the A ring ligated to at least one nucleic acid, to thereby cleave the fusion protein to release the C-terminal steroyl transferase activity in solution and covalently link the nucleophilic substituent of the A ring to the electrophilic amino acid.

It is also an object to provide a method for generating a polypeptide-nucleic acid conjugate, comprising: providing a polypeptide; providing a steroylated-nucleic acid; providing a protein catalyst adapted to link the polypeptide through a sterol moiety to the steroylated-nucleic acid; and reacting the steroylated-nucleic acid and the polypeptide, catalyzed by the protein catalyst, to form a covalently linked polypeptide-steroyl-nucleic acid conjugate.

The protein catalyst may comprise a hedgehog sterol transferase activity.

The polypeptide and the protein catalyst may be provided as a fusion protein.

The reacting may disassociate the protein catalyst from the polypeptide-nucleic acid conjugate. The protein catalyst may be linked to the polypeptide through a glycine, or other suitable electrophilic amino acid.

The fusion protein may comprise a C-terminal portion having the hedgehog sterol transferase activity, an intervening glycine, and an N-terminal portion comprising the polypeptide.

The steroylated-nucleic acid may comprise a canonical fused sterol or stanol ring system, a nucleophilic group at the 3-position of the A-ring of the fused sterol or stanol ring system. For example, beta or alpha stereochemistry ring systems may be employed, and an oligonucleotide attached through a linker to the sterol or stanol ring system, e.g., through a D-ring or other ring. The steroylated-nucleic acid may comprise at least one sterol molecule joined covalently to a nucleic acid polymer.

The polypeptide may have a length of between 2 amino acids and 500 amino acids. The polypeptide may have glycine as a last amino acid residue, linked to the protein catalyst having the hedgehog sterol transferase activity.

The protein catalyst may be of, or related to, a hedgehog-family of proteins. Homologous proteins have been identified by sequence alignments (Burglin, Thomas R. "The Hedgehog protein family." Genome biology 9, no. 11 (2008): 241, www.ncbi.nlm.nih.gov/pubmed/19040769). The protein catalyst and the polypeptide may be expressed from a genetically engineered chimeric gene. The protein catalyst and the polypeptide may be expressed from the genetically engineered chimeric gene in an organism lacking sterols. The fusion chimera polypeptide may also be produced in cell-free systems, e.g., in vitro translation. The protein catalyst may be configured to react with a last residue of the polypeptide through translation fusion. The protein catalyst may be configured to chemically link a C-terminal residue, typically glycine, of the polypeptide with the steroylated-nucleic acid. The protein catalyst may have a substrate affinity for the steroylated-nucleic acid. The protein catalyst and the polypeptide may be associated prior to the reacting, and the protein catalyst and the polypeptide may be disassociated subsequent prior to the reacting to form the polypeptide-nucleic acid conjugate.

A composition is provided according to any of the foregoing.

A kit is provided, comprising: a polypeptide comprising a C-terminal steroyl transferase activity, an N-terminal peptide, and an intervening electrophilic residue, typically glycine; and a steroylated-nucleic acid, the polypeptide and the steroylated-nucleic acid being configured to react in solution to ligate the steroylated-nucleic acid to the N-terminal peptide through the glycine, and to disassociate the C-terminal steroyl transferase activity from the ligated steroylated-nucleic acid and N-terminal peptide. The C-terminal steroyl transferase activity may correspond to a hedgehog protein steroyl transferase activity.

The polypeptide may be provided as a fusion protein expressed from a chimeric gene in a host system lacking sterols, or translated in vitro using a cell-free system.

The steroylated-nucleic acid may comprise a canonical fused sterol or stanol ring system, a nucleophilic group at the 3-position of the A-ring of the fused sterol or stanol ring system, and an oligonucleotide attached through a linker to the fused sterol or stanol ring system.

The N-terminal peptide may have a length of between 2 amino acids and 500 amino acids.

The steroylated-nucleic acid may comprise at least one sterol molecule joined covalently to a nucleic acid polymer.

It is also an object to provide a composition, comprising: a polypeptide having a C-terminal glycine, a canonical fused sterol or stanol ring system, having a nucleophilic group at the 3-position of the A-ring of the fused sterol or stanol ring system, covalently linked to the C-terminal glycine, and an oligonucleotide attached through a linker adjacent to the sterol or stanol ring system.

The polypeptide may have between 2 and 500 amino acids.

The oligonucleotide may be an RNA, single stranded DNA, a segment of a double stranded DNA, or an oligonucleotide bound to an oligonucleotide strand having a complementary sequence.

The polypeptide and/or oligonucleotide may have a therapeutic activity in an animal, a diagnostic activity in an animal, a fluorescent property, and/or a fluorescence quenching property.

A therapeutic may be provided which selectively delivers a nucleotide or oligonucleotide to cells. The nucleotide may be effective to provide gene therapy, a DNA vaccine therapy, DNA nanostructure devices, etc. In this class of applications, the linked peptide serves to target and/or anchor the nucleotide in a desired region, tissue or cell type. On the other hand, in another class of applications, the nucleotide serves the purpose of anchoring or targeting, and the peptide provides a functional therapy or function. In other cases, both the peptide and the nucleotide may have specific targeting activities or functional activities. In a still further embodiment, the ligated peptide and nucleotide is itself linked or attached to a further active or targeting functionality. For example, if the peptide is an antigen, it may be complexed with a corresponding antibody. Similarly, the nucleotide may be annealed to a corresponding antisense nucleotide. Further, the peptide may have affinity for cofactors, and thus complex with the respective cofactor and carry that to a site of action. As party of a therapy, the active molecule, which may be the fusion peptide, or the fused product, is provided in a pharmaceutically acceptable dosage form, and administered to provide an effective therapy. The disease to be treated may be a neoplastic or hyperproliferative disease, an immune disorder, a genetic disorder, a disease to be treated with a gene therapy, miRNA, siRNA, dsRNA, or other oligonucleotide therapy.

For example, the polypeptide moiety may have receptor characteristics, or receptor-specific binding characteristics, to bind to a corresponding receptor or ligand on or in a specific tissue. The binding may lead to an endycytosis of the oligonucleotide, and thus obtain cell entry. The oligonucleotide may then act within the endocytosed environment, be released from the endosome into the cell, or the peptide-steroyl-oligonucleotide may act to lyse the endosome. In other cases, the peptide or oligonucleotide may act at the cell surface, external to the cell.

At least one of the polypeptide and the oligonucleotide may be bound to a support or a suspended particle.

The polypeptide may be configured to act as a sensor to report a presence and/or concentration of an analyte, as shown in FIGS. 6B and 6C. As shown in FIG. 6B, the analyte is lead, which alters a configuration of a strand of DNA into a quadruplex formation. As shown in FIG. 6C, the analyte is pathogen DNA, which is sensed by an antisense oligonucleotide strand linked to a nanoluciferase peptide. In an absence of pathogen DNA, the luciferase luminescence is quenched by a DABCYL (4-((4-(dimethylamino)phenyl) azo)benzoic Acid, www.thermofisher.com/order/catalog/product/D2245), while in the presence of the pathogen DNA, the quencher is displaced from the nanoluciferase, and luminescence is apparent.

The polypeptide may be configured to act as an antigen for a corresponding antibody, or an antigen binding domain of an antibody.

The polypeptide may comprise a protease-sensitive domain, configured to release the oligonucleotide in response to cleavage of the protease-sensitive domain by a protease, as shown in FIG. 7. The oligonucleotide may comprise a restriction endonuclease-sensitive domain, configured to release a portion of the oligonucleotide in response to cleavage of the restriction endonuclease-sensitive domain by a corresponding protease restriction endonuclease.

The polypeptide may comprise a receptor binding domain, configured to deliver the oligonucleotide to a specific cell type by receptor-mediated endocytosis, also shown in FIG. 7. The oligonucleotide may comprise biologically active oligonucleotide, such as a DNAzyme, or siRNA, or the nucleic acid that has a specific target within the cell.

These and other objects will become apparent from a review of the description herein.

BRIEF DESCRIPTION OF FIGURES

FIGS. 5A-5C show, respectively, conjugation of an oligonucleotide (or other ligand) to a bead, an antibody, and to a cell surface.

FIG. 6A shows a general scheme for creating enzyme-aptamer conjugates.

FIG. 6B shows a strand-to-quadraplex sensor for bioluminescence resonance energy transfer (BRET), for lead sensing.

FIG. 6C shows a hairpin-to-rod sensor for pathogen DNA with accompanying fluorescent enhancement.

DETAILED DESCRIPTION OF THE PREFERRED EMBODIMENT

According to one embodiment, the technology provides a method of conjugating a protein to a steroylated-oligonucleotide.

Figure 1:
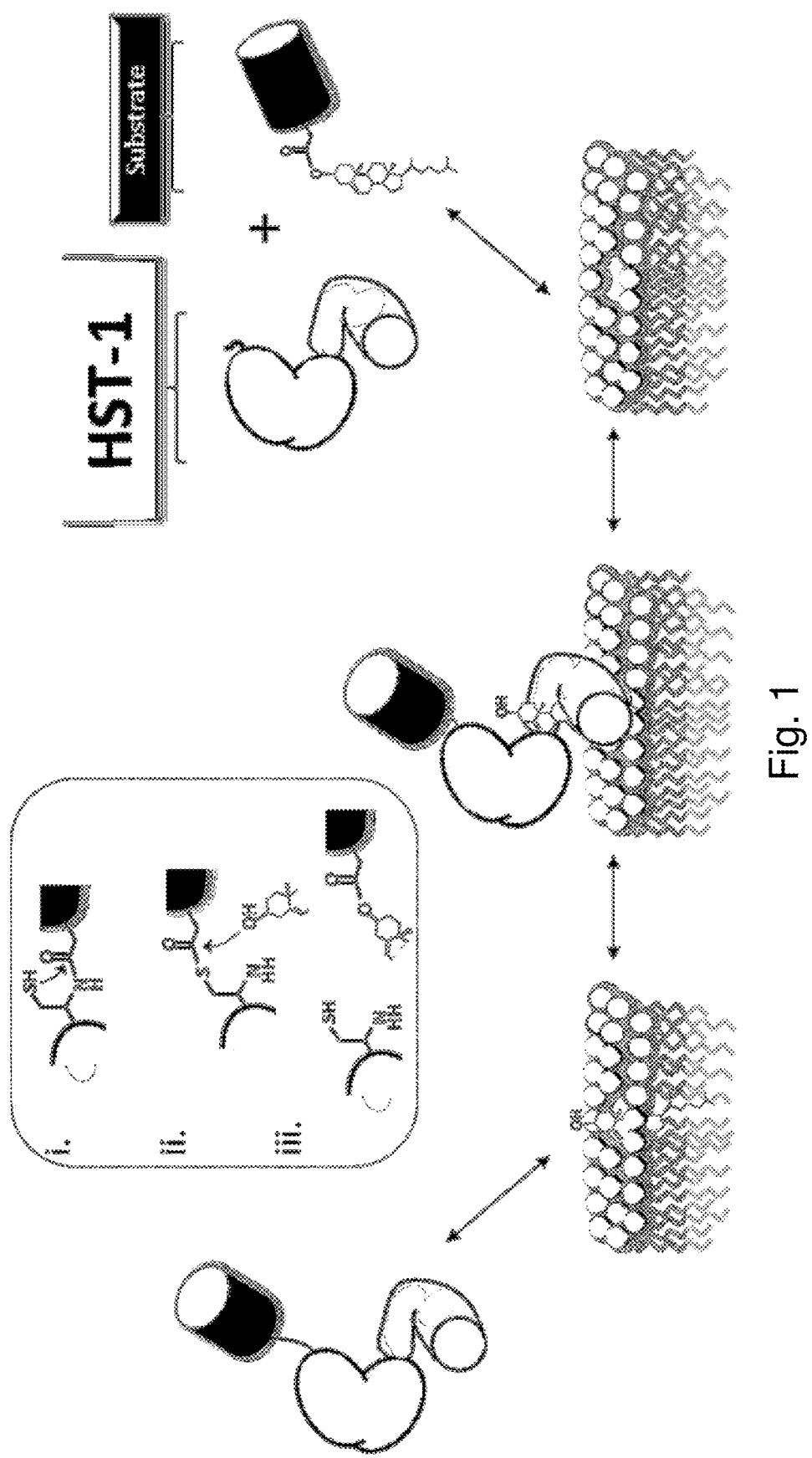
FIG. 1 shows the native conjugation activity of HST-I.

FIG. 1 shows the native conjugation activity of HST-I. A hedgehog precursor protein comprised of HhN linked to the HST-I polypeptide, associates with cholesterol in a cellular membrane; membrane bound HST-I generates an internal thioester by rearranging the peptide bond at the HhN/HST-I junction; HST-I then activates a molecule of cholesterol to attack the internal thioester, resulting in the departure of HhN and the linking of HhN to cholesterol as a carboxyl ester.

Chemical Synthesis of Steroylated-Oligonucleotide

Figure 2:
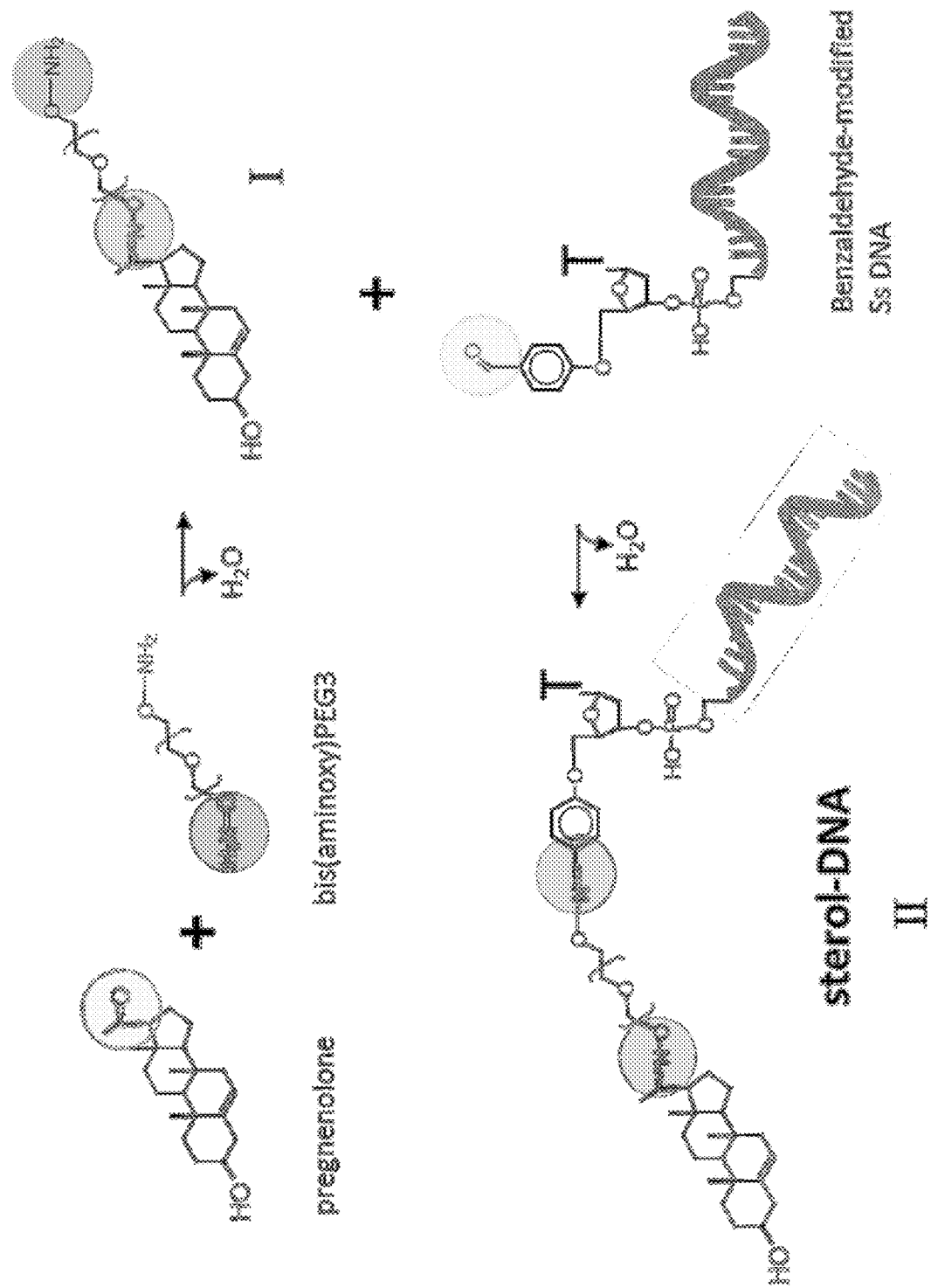
FIG. 2 shows steroylated-oligonucleotides suitable for HST-I catalyzed conjugation.
Figure 3A:
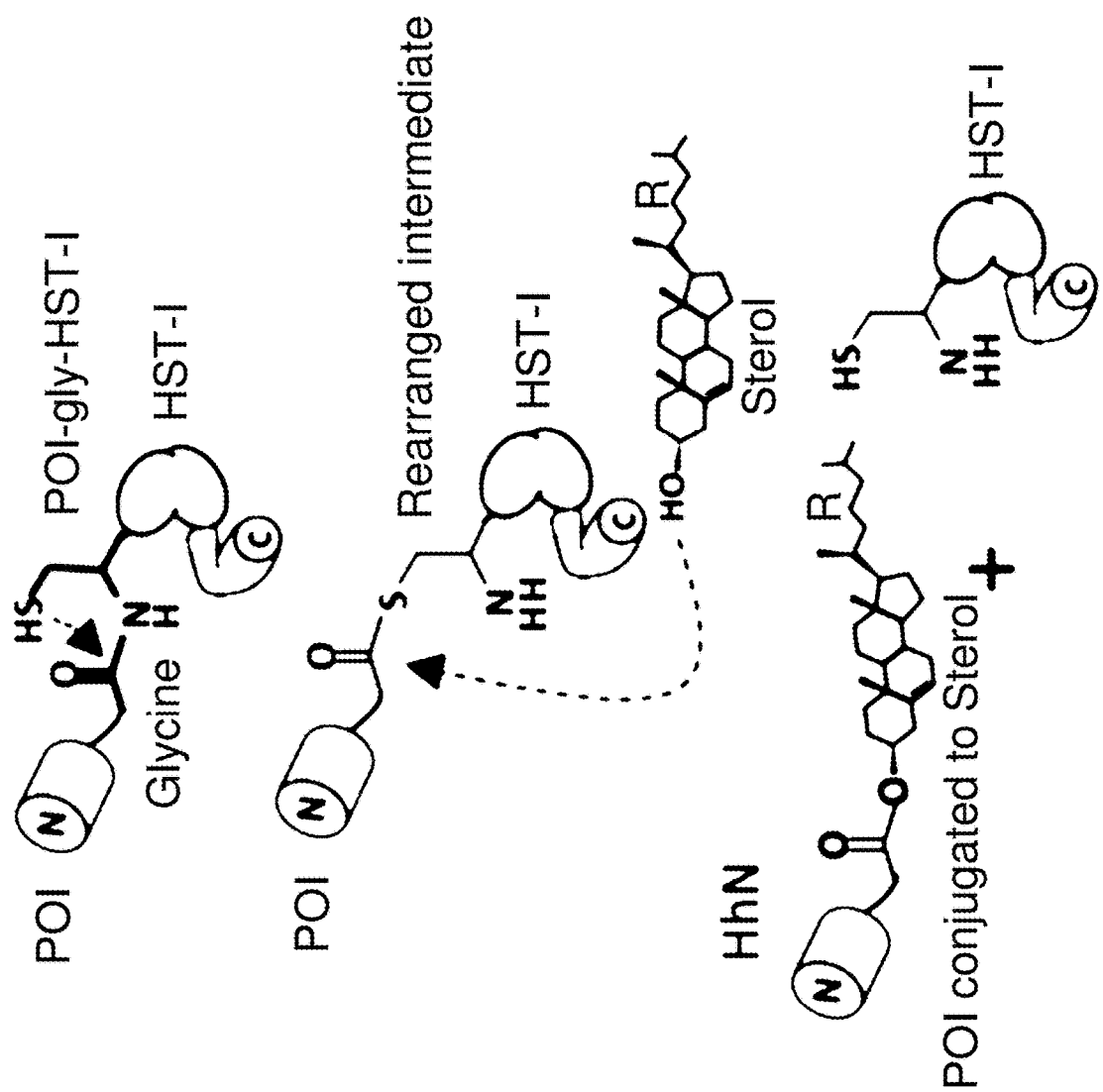
FIGS. 3A and 3B show results of a study which conjugates proteins to oligonucleotides using HST-I.
Figure 3B:
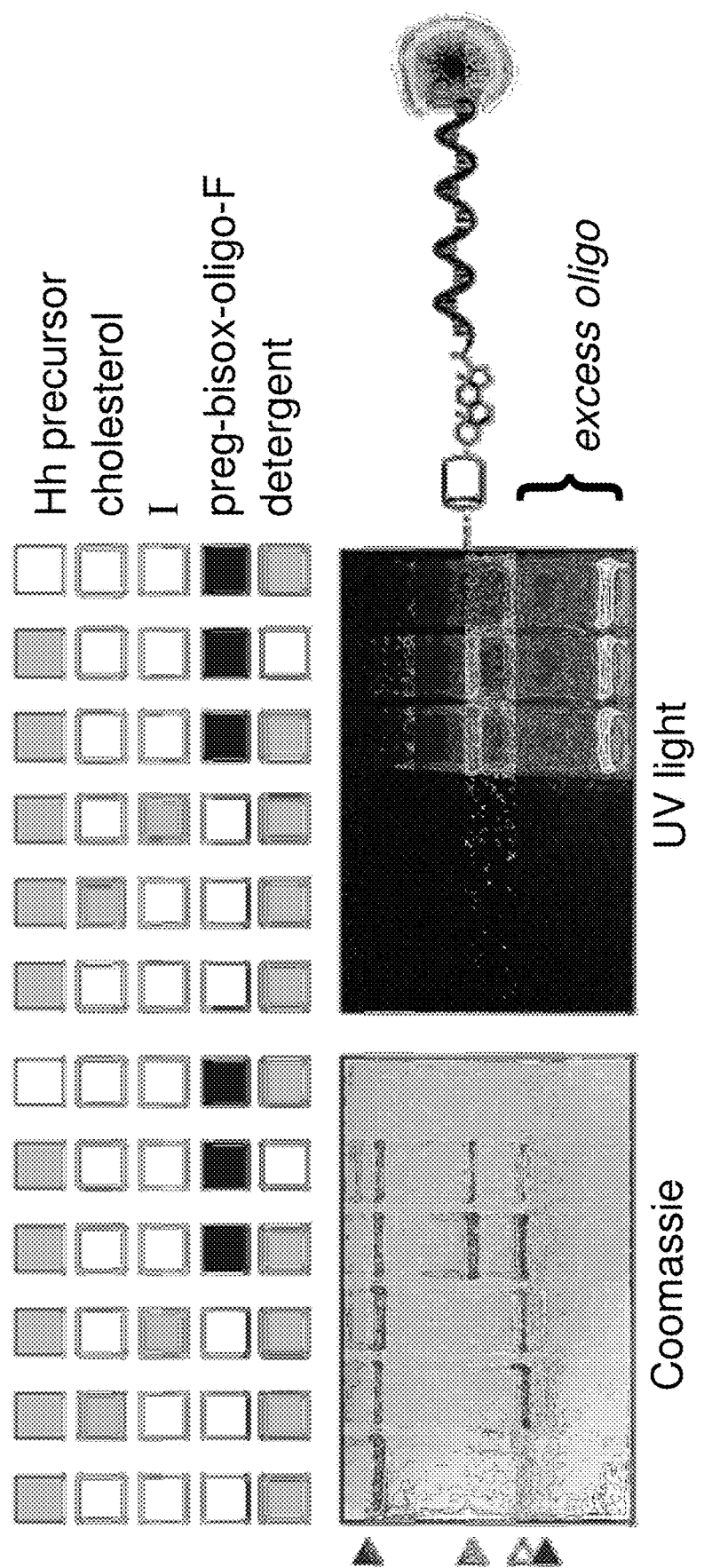
Figure 4:
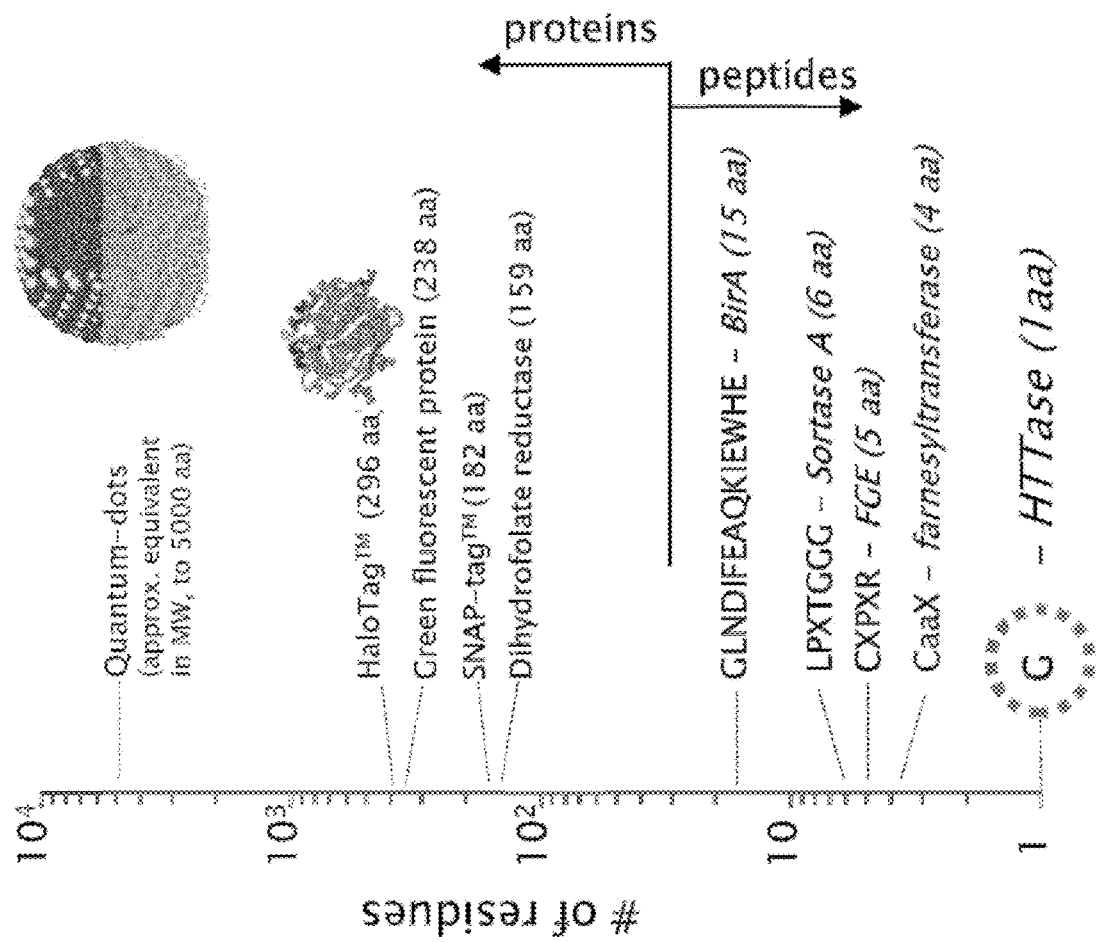
FIG. 4 shows that, compared to other biocatalytic conjugations, HST-I leaves the smallest residual sequence "scar".
Figure 7:
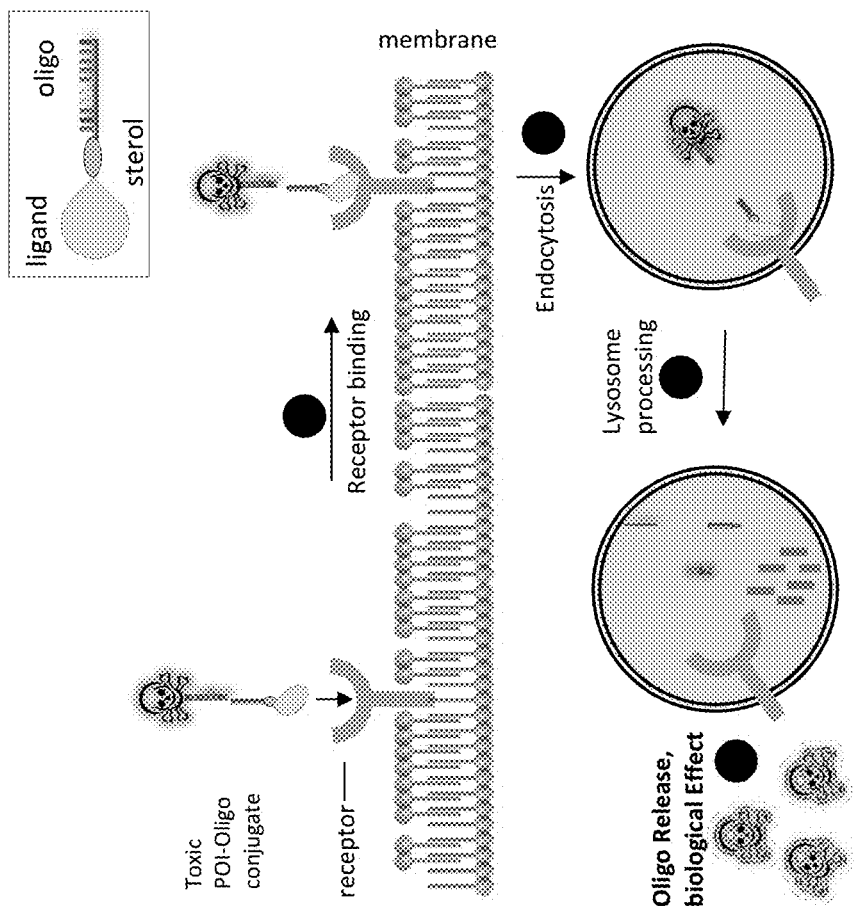
FIG. 7 shows receptor specific binding of protein-oligonucleotide conjugates.

A nominal 2-step protocol is provided to synthesize sterol-oligonucleotides via oxime chemistry, as shown schematically in FIG. 2.

The protocol takes advantage of the fact that aminooxy groups react to form oximes in buffered aqueous conditions with equilibrium constants, typically in the range of $>10^8$ $M^{-1}$. Sterol-oligonucleotides compatible with HST-I catalyzed conjugation generally have the same general structure as (II) shown in FIG. 2, namely, a canonical fused sterol or stanol ring system, a nucleophilic group at the 3-position of the A-ring with beta stereochemistry, and an oligonucleotide attached through a linker adjacent to the D ring.

FIG. 2 shows that steroylated-oligonucleotides suitable for HST-I catalyzed conjugation can be synthesized by sequential oxime formation chemistry. The reaction sequence begins with the reaction of pregnenolone and bis(aminoxy)PEG3 to form intermediate (I); followed by reaction of I with benzaldehyde modified oligonucleotide to form II.

The reaction proceeds as follows:

Pregnenolone-16-ene oxime (PEG3) aminoxy (I): In a total volume of 1 ml consisting of 900 µl MeOH/100 µl triethanolamine acetate buffer (1 M, pH 7), dissolve 0.2 mmoles of Bis-(Aminooxy)-PEG3 with 0.1 mmoles of pregnenolone. Solution starts out cloudy, then turns clear after overnight mixing on a vortex. Oxime formation is monitored by TLC (95% Dichloromethane/5% methanol). Product, pregnonlone is isolated by organic extraction (3x) using 6 mls ethylacetate/6 mls water, followed by drying under nitrogen stream to a white solid. Typical yield is 70-85%.

Pregnenolone-16-ene bisoxime(PEG3)-oligo-dT20 (II): In microscale reaction, the product from step (I) is joined using the same oxime chemistry to an oligonucleotide equipped with a (4-formylbenzamide) group, obtained commercially (Solulink/TriLink Inc.). The solvent is 90/10, methanol/triethanolmamine acetate buffer (pH 7), with I at 0.02 M and the oligonucleotide 0.0002 M. Following overnight incubation, the sterol-oligonucleotide (II) is purified using microspin oligo clean and concentrator column (Zymogen Inc.), and eluted with water.

Fusion Protein

Create and Clone a Synthetic Gene Encoding POI Fused to HST-I.

The gene encoding the protein of interest (POI) is cloned into an expression plasmid, creating an in-frame translational fusion with HST-I. If the last amino acid of the target protein is not glycine, a glycine codon is added at the 3' of the POI gene. This step involves standard molecular biology techniques.

Express POI-HST-I Fusion Protein.

Recombinant vector encoding POI-HST-I fusion protein is transformed into a suitable expression host, e.g., *E. coli*, strain BL21 DE3.

Alternative hosts, ideally organisms that do not contain endogenous sterols, may be employed. Endogenous sterols may react with the POI-HST-I precursor protein, resulting in the release of POI.

It is also possible to produce the POI-HST-I fusion peptide by in vitro translation. See, www.neb.com/tools-and-resources/feature-articles/the-next-generation-of-cell-free-protein-synthesis; www.thermofisher.com/us/en/home/references/ambion-tech-support/large-scale-transcription/general-articles/the-basics-in-vitro-translation.html; en.wikipedia.org/wiki/Cell-free_protein_synthesis; Mikami S et al. (2006) A hybridoma-based in vitro translation system that efficiently synthesizes glycoproteins. J Biotechnol 127 (1):65-78; Mikami S et al. (2006) An efficient mammalian cell-free translation system supplemented with translation factors. Protein Expr Purif 46(2):348-57.

Purify POI-HST-1 Fusion Protein.

Fusion protein is purified from the cell extract using an appropriate chromatography method. For example, immobilized metal affinity chromatography may be used (IMAC). Other purification techniques (GST-tag; chitin-tag; MBP-tag) could also be used.

Conjugation

Conjugation of POI to the sterol-oligonucleotide through the action of HST-I is initiated at room temperature by addition of a sterol-oligonucleotide to a final concentration 100-200 μM. Progress of the reaction can be followed by a variety of analytical methods. For example, SDS-PAGE may be used to monitor the change in molecular weight as the POI is conjugated and released from HST-1.

A final chromatography step can be carried out to separate HST-I from the conjugated target protein.

Example

The feasibility of HST-I catalyzed conjugation of protein to nucleic acids has been assessed through pilot scale experiments. In one example, a chimeric gene encoding a 20 kDa POI fused to HST-1 was created. This gene product, a 46 kDa precursor polypeptide, was expressed in *E. coli* and purified under native conditions using immobilized metal affinity chromatography. To test conjugation activity, a 30 μl solution of the purified protein (2 μM, final) in BisTris buffered solution, was mixed with sterol-oligonucleotide (~35 μM, final).

The oligonucleotide used in this experiment was chemically modified with a fluorescein group. After 3 hours at room temperature, contents of the reaction and control reactions were separated by SDS-PAGE. The gel was first imaged using UV light source to detect the fluorescent oligonucleotide, and then by Coomassie staining which detects all proteins, as shown in FIGS. 3A and 3B.

FIGS. 3A and 3B show results of a pilot study which establishes feasibility of conjugating proteins to oligonucleotides using HST-I. FIG. 3A shows a scheme for the conjugation activity of POI-HST-I precursor protein. FIG. 3B shows conjugation of 46 kDa POI-HST-I fusion protein with sterol-oligonucleotide. Images of gels following SDS-PAGE to resolve reactions of POI-HST-I in the absence (lane 1) and presence of cholesterol (lane 2), synthetic sterol (lane 3), and a synthetic sterol-oligonucleotide. The gel was imaged under UV light (right) to detect the oligonucleotide, which was equipped with a fluorescein molecule; and under white light following straining with Coomassie dye (left).

Symbols:

POI-HST-I precursor protein (top triangles);

The POI-sterol-DNA conjugate (next-to-top triangle);

HST-I protein, released by conjugation, (next-to bottom triangles);

The sterol-modified POI (bottom triangles).

FIG. 4 shows that, compared to other biocatalytic conjugations, HST-I leaves the smallest residual sequence "scar".

FIGS. 5A-5C show, respectively, conjugation of an oligonucleotide (or other ligand) to a bead, an antibody, and to a cell surface.

FIG. 6A shows a general scheme for creating enzyme-aptamer conjugates.

FIG. 6B shows a strand-to-quadraplex sensor for bioluminescence resonance energy transfer (BRET), for lead sensing, which exploits the ability of certain DNA to form a quadraplex with $Pb^{2+}$ ions, which brings a dye, e.g., alexfluor 610 in close proximity to a nanoluciferase peptide.

FIG. 6C shows a hairpin-to-rod sensor for pathogen DNA, which exploits the ability of DABCYL to quench nanoluciferase when in close proximity, but to permit luminescence when displaced, such as during a hairpin-to-rod transformation or DNA or RNA.

FIG. 7 shows receptor specific binding of protein-oligonucleotide conjugates. In this case, FIG. 7 proposes a toxin ligated to the oligonucleotide, which is then endocytosed, and processed with lysosomes by normal cell activity, to release the toxin.

In the sample containing the HST-I precursor protein, conjugation activity is indicated by the diminished staining of the precursor protein compared with control, as well as by the appearance of protein corresponding to the molecular weight of HST-I. Finally, in this sample, a high molecular weight product (dots) is observed that reacts with the Coomassie stain and gives off a fluorescence signal. Together, these characteristics indicate that this species is the desired protein-oligonucleotide conjugate.

Each reference cited herein is expressly incorporated herein by reference it its entirety.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and the figures included herein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

What is claimed is:

1. A composition, comprising:
   a conjugate reaction product of:
   a polypeptide having a C-terminal electrophilic residue,
   a fused sterol or stanol ring system, having a nucleophilic group at the 3-position of an A-ring of the fused sterol or stanol ring system with beta or alpha stereochemistry, covalently linked to the C-terminal electrophilic residue, and
   an oligonucleotide attached through a linker to a ring of the fused sterol or stanol ring system.

2. The composition according to claim 1, wherein the electrophilic residue comprises glycine.

3. The composition according to claim 1, wherein the oligonucleotide is RNA.

4. The composition according to claim 1, wherein the oligonucleotide is DNA.

5. The composition according to claim 1, in a pharmaceutically acceptable dosage form for administration to a human.

6. The composition according to claim 1, having at least one of therapeutic activity and diagnostic functionality, in an animal.

7. The composition according to claim 1, configured to act as a sensor to report a presence of an analyte.

8. The composition according to claim 1, wherein the polypeptide comprises a protease-sensitive domain, adapted to be cleaved by a mammalian sequence-specific protease.

9. A composition, comprising:
   a conjugate reaction product of:
   a fused sterol or stanol ring system, having a nucleophilic group at the 3-position of an A-ring of the fused sterol or stanol ring system with beta or alpha stereochemistry;
   a polypeptide, covalently linked through a C-terminal electrophilic residue to the fused sterol or stanol ring system; and
   an oligonucleotide attached through a linker to the fused sterol or stanol ring system.

10. The composition according to claim 9, wherein the peptide comprises a receptor binding domain.

11. The composition according to claim 9, wherein the peptide comprises a protease sensitive domain, adapted to be cleaved by a mammalian sequence-specific protease.

12. The composition according to claim 9, wherein the peptide comprises at least one of an antigen and an antigen-binding domain of an antibody.

13. The composition according to claim 9, wherein the C-terminal electrophilic residue comprises glycine.

14. The composition according to claim 9, wherein the oligonucleotide comprises a restriction endonuclease-sensitive domain.

15. A composition, comprising a conjugate reaction product of:
   a polypeptide having a C-terminal electrophilic residue,
   a fused sterol or stanol ring system, having a nucleophilic group at the 3-position of an A-ring of the fused sterol or stanol ring system with beta or alpha stereochemistry, covalently linked to the C-terminal electrophilic residue, and
   an oligonucleotide attached through a linker to a ring of the fused sterol or stanol ring system,
   prepared by a method comprising:
   providing a precursor polypeptide;
   providing the oligonucleotide attached through the linker to the ring of the fused sterol or stanol ring system;
   providing a protein catalyst adapted to link the precursor polypeptide to the steroylated or stanoylated-nucleic acid through a sterol or stanol moiety of the steroylated or stanoylated-nucleic acid; and
   reacting the steroylated or stanoylated-nucleic acid and the precursor polypeptide, catalyzed by the protein catalyst, to form the composition.

16. The composition according to claim 15, wherein the protein catalyst comprises a hedgehog sterol transferase activity.

17. The composition according to claim 16, wherein the precursor polypeptide and the protein catalyst are provided as a fusion protein.

18. The composition according to claim 17, wherein the precursor polypeptide has glycine as a last amino acid residue, linked to the protein catalyst having the hedgehog sterol transferase activity.

19. The composition according to claim 17, wherein said reacting disassociates the protein catalyst from the polypeptide-nucleic acid conjugate.

20. The composition according to claim 19, wherein the protein catalyst is linked to the precursor polypeptide through the C-terminal electrophilic residue of the precursor polypeptide.

21. The composition according to claim 20, wherein the fusion protein comprises a C-terminal portion having the hedgehog sterol transferase activity, an intervening electrophilic residue, and an N-terminal portion comprising the precursor polypeptide.

22. The composition according to claim 15, wherein the precursor polypeptide has a length of between 2 amino acids and 500 amino acids.

23. The composition according to claim 15, wherein the protein catalyst is configured to react with a last residue of the precursor polypeptide through translation fusion.

24. The composition according to claim 15, wherein the protein catalyst is configured to chemically link a C-terminal glycine residue of the precursor polypeptide with the steroylated-nucleic acid.

* * * * *

SEQUENCE LISTING

```
<160> NUMBER OF SEQ ID NOS: 1

<210> SEQ ID NO 1
<211> LENGTH: 215
<212> TYPE: PRT
<213> ORGANISM: Drosophila melanogaster

<400> SEQUENCE: 1

Gly Cys Phe Thr Pro Glu Ser Thr Ala Leu Leu Glu Ser Gly Val Arg
1               5                   10                  15

Lys Pro Leu Gly Glu Leu Ser Ile Gly Asp Arg Val Leu Ser Met Thr
            20                  25                  30

Ala Asn Gly Gln Ala Val Tyr Ser Glu Val Ile Leu Phe Met Asp Arg
        35                  40                  45

Asn Leu Glu Gln Met Gln Asn Phe Val Gln Leu His Thr Asp Gly Gly
    50                  55                  60

Ala Val Leu Thr Val Thr Pro Ala His Leu Val Ser Val Trp Gln Pro
65                  70                  75                  80

Glu Ser Gln Lys Leu Thr Phe Val Phe Ala Asp Arg Ile Glu Glu Lys
                85                  90                  95

Asn Gln Val Leu Val Arg Asp Val Glu Thr Gly Glu Leu Arg Pro Gln
            100                 105                 110

Arg Val Val Lys Val Gly Ser Val Arg Ser Lys Gly Val Val Ala Pro
        115                 120                 125

Leu Thr Arg Glu Gly Thr Ile Val Val Asn Ser Val Ala Ala Ser Cys
    130                 135                 140

Tyr Ala Val Ile Asn Ser Gln Ser Leu Ala His Trp Gly Leu Ala Pro
145                 150                 155                 160

Met Arg Leu Leu Ser Thr Leu Glu Ala Trp Leu Pro Ala Lys Glu Gln
                165                 170                 175

Leu His Ser Ser Pro Lys Val Val Ser Ser Ala Gln Gln Gln Asn Gly
            180                 185                 190

Ile His Trp Tyr Ala Asn Ala Leu Tyr Lys Val Lys Asp Tyr Val Leu
        195                 200                 205

Pro Gln Ser Trp Arg His Asp
    210                 215
```